(12) United States Patent
Oosake

(10) Patent No.: US 11,298,012 B2
(45) Date of Patent: Apr. 12, 2022

(54) IMAGE PROCESSING DEVICE, ENDOSCOPE SYSTEM, IMAGE PROCESSING METHOD, AND PROGRAM

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/901,017

(22) Filed: Jun. 15, 2020

(65) Prior Publication Data

US 2020/0305698 A1 Oct. 1, 2020

Related U.S. Application Data

(63) Continuation of application No. PCT/JP2018/043138, filed on Nov. 22, 2018.

(30) Foreign Application Priority Data

Dec. 26, 2017 (JP) .............................. JP2017-249071

(51) Int. Cl.
*A61B 1/045* (2006.01)
*A61B 1/06* (2006.01)
(Continued)

(52) U.S. Cl.
CPC .............. *A61B 1/045* (2013.01); *A61B 1/063* (2013.01); *G02B 23/24* (2013.01); *G06T 7/0012* (2013.01);
(Continued)

(58) Field of Classification Search
CPC ..... A61B 1/045; A61B 1/063; A61B 1/00009; G02B 23/24; G06T 7/0012;
(Continued)

(56) References Cited

U.S. PATENT DOCUMENTS

| 6,597,934 B1 | 7/2003 | de Jong et al. |
| 2007/0195165 A1 | 8/2007 | Hirakawa |
| 2016/0027175 A1* | 1/2016 | Kim ...................... G06T 7/0016 382/131 |

FOREIGN PATENT DOCUMENTS

| JP | 2001285677 | 10/2001 |
| JP | 2004518472 | 6/2004 |

(Continued)

OTHER PUBLICATIONS

"International Search Report (Form PCT/ISA/210) of PCT/JP2018/043138," dated Feb. 19, 2019, with English translation thereof, pp. 1-5.

(Continued)

*Primary Examiner* — James M Pontius
(74) *Attorney, Agent, or Firm* — JCIPRNET

(57) ABSTRACT

Provided are an image processing device, an endoscope system, an image processing method, and a program capable of automatically differentiating a medical image including a scene of interest and supporting saving of the medical image according to a differentiation result.

The image processing device includes a medical image acquisition unit (41) that acquires a medical image, a scene-of-interest recognition unit (51) that recognizes a scene of interest from the medical image acquired using the medical image acquisition unit, a degree-of-similarity calculation unit (52) that, for the scene of interest recognized using the scene-of-interest recognition unit, calculates a degree of similarity between the medical image acquired using the medical image acquisition unit and a standard image determined for the scene of interest, and a saving processing unit (53) that executes processing for saving the medical image in a saving device based on the degree of similarity calculated using the degree-of-similarity calculation unit.

15 Claims, 12 Drawing Sheets

(51) Int. Cl.
*G02B 23/24* (2006.01)
*G06T 7/00* (2017.01)

(52) U.S. Cl.
CPC ........... *G06T 2207/10068* (2013.01); *G06T 2207/30004* (2013.01)

(58) Field of Classification Search
CPC . G06T 2207/10068; G06T 2207/30004; G06T 2207/30032; G06T 2207/30096; G06T 2207/20084; G06T 7/0014
See application file for complete search history.

(56) References Cited

FOREIGN PATENT DOCUMENTS

| JP | 2012005512 | 1/2012 |
| JP | 5157704 | 3/2013 |
| JP | 2013200590 | 10/2013 |
| WO | 2017073337 | 5/2017 |

OTHER PUBLICATIONS

"Written Opinion of the International Searching Authority (Form PCT/ISA/237) of PCT/JP2018/043138," dated Feb. 19, 2019, with English translation thereof, pp. 1-10.

Yamada Masayoshi, et al., "Development of real-time endoscopic image automatic analysis system for finding colorectal cancer and pre-cancerous lesions using an artificial intelligence system based on quantification of shape information," Nippon Shokakibyo Gakkai Zasshi, vol. 114 special extra edition (conference), Sep. 2017, pp. 1.

Office Action of Japan Counterpart Application, with English translation thereof, dated Feb. 10, 2021, pp. 1-8.

* cited by examiner

IMAGE PROCESSING DEVICE, ENDOSCOPE SYSTEM, IMAGE PROCESSING METHOD, AND PROGRAM

CROSS-REFERENCE TO RELATED APPLICATIONS

The present application is a Continuation of PCT International Application No. PCT/JP2018/043138 filed on Nov. 22, 2018 claiming priority under 35 U.S.C § 119(a) to Japanese Patent Application No. 2017-249071 filed on Dec. 26, 2017. Each of the above applications is hereby expressly incorporated by reference, in its entirety, into the present application.

BACKGROUND OF THE INVENTION

1. Field of the Invention

The present invention relates to an image processing device, an endoscope system, an image processing method, and a program, and in particular, to saving of a medical image.

2. Description of the Related Art

In a medical field, inspection using an endoscope device has been performed. In recent years, a system that recognizes a lesion included in an endoscope image as an observation image of an endoscope using image analysis is known. In an endoscopy, manipulation and observation need to be simultaneously performed. For example, in a case where eyes are turned to an operating part in performing manipulation, oversight of a lesion, erroneous determination, or the like may occur. There is a need for support to suppress oversight of a lesion or the like.

In the image analysis for lesion recognition, machine learning of an image including deep learning has been widely used. A machine learning device needs to collect data for learning for use in performing machine learning. In general, the machine learning device needs a large number of pieces of data for learning. For this reason, the number of pieces of data for learning that is collected in the machine learning device becomes extremely large.

WO2017/073337A describes an endoscope device that acquires an endoscope image of a subject, detects a lesion part from the acquired endoscope image, and in a case where the lesion part is detected, gives notification and highlights the lesion part. The endoscope device described in the document extracts a feature quantity from the endoscope image, compares a feature quantity of polyp model information stored in advance with the feature quantity of the endoscope image, and in a case where the feature quantities coincide with each other, detects the lesion part.

JP2012-005512A describes an image processing device that detects a lesion from a second image as a captured image of a scope type endoscope using a feature quantity of a first image output from a capsule endoscope. The image processing device described in the document calculates a standard feature quantity based on a pixel value of a pixel in the first image and detects a part of interest from the second image based on the standard feature quantity and a pixel value of the second image.

JP5157704B describes an electronic still camera detects an expression of a face and starts continuous imaging according to a determination result corresponding to an expression level indicating the degree of expression.

SUMMARY OF THE INVENTION

However, there is a need for automatically differentiating a lot of medical images and supporting saving of the medical images according to a differentiation result in using a medical image.

In the invention described in WO2017/073337A, in a case where a lesion part candidate is detected from the endoscope image, a marker image is attached to a static image, and the static image with the marker image is displayed using a display unit. On the other hand, in the invention described in WO2017/073337A, the static image is primarily stored in order to display the static image; however, WO2017/073337A has no description relating to saving of a static image in a storage device.

In the invention described in JP2012-005512A, a threshold value for use in extracting the part of interest can be changed according to a kind of part of interest to support the extraction of the part of interest; however, in the invention described in JP2012-005512A, there is no description that an image where a part of interest is extracted is differentiated and saved according to a differentiation result.

In the invention described in JP5157704B, continuously captured images are saved in a common folder, and there is no description that continuously captured images are differentiated and saved based on a differentiation result.

The invention has been accomplished in view of such circumstances, and an object of the invention is to provide an image processing device, an endoscope system, an image processing method, and a program capable of automatically differentiating a medical image including a scene of interest and supporting saving of the medical image according to a differentiation result.

In order to achieve the above-described object, the invention provides the following aspects.

According to a first aspect, there is provided an image processing device comprising a medical image acquisition unit that acquires a medical image, a scene-of-interest recognition unit that recognizes a scene of interest from the medical image acquired using the medical image acquisition unit, a degree-of-similarity calculation unit that, for the scene of interest recognized using the scene-of-interest recognition unit, calculates a degree of similarity between the medical image acquired using the medical image acquisition unit and a standard image determined for the scene of interest, and a saving processing unit that performs processing for saving the medical image in a saving device based on the degree of similarity calculated using the degree-of-similarity calculation unit.

According to the first aspect, the medical image where the scene of interest is recognized is acquired and saved according to the degree of similarity with the standard image. With this, it is possible to automatically differentiate the medical image where the scene of interest is recognized and to save the medical image according to a differentiation result.

An example of the medical image is an endoscope image that is an observation image of an endoscope. The endoscope image may be video or time-series static images.

In a case where the medical image is video, as the medical image where the scene of interest is recognized, one or more frame images within a given period from a timing when the scene of interest is recognized may be saved.

The scene of interest may be composed of one image or may be composed of an image group including a plurality of images. An example of a feature included in the scene of interest, a lesion is a state of a lesion, or the like.

According to a second aspect, the image processing device of the first aspect may further comprise a medical image feature quantity extraction unit that extracts a feature quantity from the medical image, and the degree-of-similarity calculation unit may calculate the degree of similarity between the medical image and the standard image based on the feature quantity of the medical image.

According to the second aspect, it is possible to save the medical image based on the degree of similarity according to the feature quantity of the medical image.

According to a third aspect, the image processing device of the first aspect or the second aspect may further comprise a standard image acquisition unit that acquires the standard image, and a standard image feature quantity extraction unit that extracts a feature quantity from the standard image acquired using the standard image acquisition unit.

According to the third aspect, it is possible to save the medical image based on the degree of similarity according to the feature quantity of the standard image.

According to a fourth aspect, the image processing device of the first aspect or the second aspect may further comprise a standard image feature quantity acquisition unit that acquires a feature quantity of the standard image, and the degree-of-similarity calculation unit may calculate the degree of similarity between the medical image and the standard image based on a feature quantity of the medical image and the feature quantity of the standard image.

According to the fourth aspect, it is possible to save the medical image based on the degree of similarity according to the feature quantity of the medical image and the feature quantity of the standard image.

A concept of the acquisition of the feature quantity of the standard image may include an aspect where the feature quantity is extracted from the standard image, and the extracted feature quantity is acquired.

According to a fifth aspect, in the image processing device of any one aspect of the first aspect to the fourth aspects, the scene-of-interest recognition unit may recognize a scene including a lesion as the scene of interest.

According to the fifth aspect, it is possible to recognize the scene of interest including the lesion from the medical image.

According to a sixth aspect, in the image processing device of any one aspect of the first aspect to the fifth aspect, the scene-of-interest recognition unit may acquire a plurality of medical images from a medical image saving device, in which the plurality of medical images are saved in advance, may recognize a scene of interest for the plurality of medical images, and may select the standard image hardly recognized by the scene-of-interest recognition unit from among medical images unrecognized as the scene of interest, and the saving processing unit may save the medical image in the saving device in a case where the degree of similarity is equal to or greater than a prescribed threshold value.

According to the sixth aspect, it is possible to automatically differentiate the medical image similar to the standard image hardly recognized by the scene-of-interest recognition unit and save the medical image according to the differentiation result.

According to a seventh aspect, in the image processing device of the sixth aspect, the scene-of-interest recognition unit may select the standard image from among medical images unrecognized as the scene of interest using a comparison result of the medical image unrecognized as the scene of interest by the scene-of-interest recognition unit and a correct answer image of a medical image hardly recognized by the scene-of-interest recognition unit, and the saving processing unit may save the medical image in the saving device in a case where the degree of similarity is equal to or greater than the prescribed threshold value.

According to the seventh aspect, it is possible to automatically differentiate the medical image similar to the standard image based on the correct answer image of the medical image hardly recognized by the scene-of-interest recognition unit and to save the medical image according to a differentiation result.

According to an eighth aspect, in the image processing device of any one aspect of the first aspect to the fifth aspect, the scene-of-interest recognition unit may recognize the scene of interest from the medical image, and the saving processing unit may save the medical image in the saving device in a case where the degree of similarity is equal to or less than a prescribed threshold value with the medical image already saved in the saving device as a standard image.

According to the eighth aspect, it is possible to save the medical image dissimilar to the previously saved medical image among the medical images recognized as the scene of interest.

According to a ninth aspect, the image processing device of the eighth aspect may further comprise an imaging mode switching signal transmission unit that transmits a switching signal for switching an imaging mode of an endoscope from a video imaging mode to a static image capturing mode to an endoscope device comprising the endoscope in a case where the scene of interest is recognized.

According to the ninth aspect, it is possible to automatically image the static image of the scene of interest in a case where the scene of interest is recognized.

According to a tenth aspect, in the image processing device of the eighth aspect or the ninth aspect, the saving processing unit may save the medical image recognized as the scene of interest in the saving device.

According to the tenth aspect, it is possible to save the medical image recognized as the scene of interest.

According to an eleventh aspect, in the image processing device of the eighth aspect or the ninth aspect, the saving processing unit may save the medical image acquired after the medical image recognized as the scene of interest in the saving device.

According to the eleventh aspect, it is possible to save the medical image acquired after the medical image recognized as the scene of interest as the medical image recognized as the scene of interest.

According to a twelfth aspect, the image processing device of any one aspect of the eighth aspect to the eleventh aspect may further comprise a standard image setting unit that sets a first medical image recognized as the scene of interest using the scene-of-interest recognition unit as the standard image.

According to the twelfth aspect, it is possible to automatically differentiate the medical image dissimilar to the first medical image recognized as the scene of interest and to save the medical image according to a differentiation result.

According to a thirteenth aspect, the image processing device of any one aspect of the first aspect to the twelfth aspect may further comprise a notification unit that gives notification of saving of the medical image in the saving device.

According to the thirteenth aspect, saving of the medical image recognized as the scene of interest is notified. With this, a practitioner can ascertain saving of the medical image recognized as the scene of interest.

According to a fourteenth aspect, there is provided an endoscope system comprising an endoscope device that comprises an endoscope, and an image processing device. The image processing device comprises a medical image acquisition unit that acquires a medical image, a scene-of-interest recognition unit that recognizes a scene of interest from the medical image acquired using the medical image acquisition unit, a degree-of-similarity calculation unit that, for the scene of interest recognized using the scene-of-interest recognition unit, calculates a degree of similarity between the medical image acquired using the medical image acquisition unit and a standard image determined for the scene of interest, and a saving processing unit that performs processing for saving the medical image in a saving device based on the degree of similarity calculated using the degree-of-similarity calculation unit.

According to the fourteenth aspect, it is possible to obtain the same effects as in the first aspect.

In the fourteenth aspect, the same matters as the matters specified in the second aspect to the thirteenth aspect can be combined as appropriate. In this case, the components that perform processing or functions specified in the image processing device can be ascertained as the components of the endoscope system that performs corresponding processing or functions.

According to a fifteenth aspect, the endoscope system of the fourteenth aspect may further comprise a saving device that saves the medical image.

According to the fifteenth aspect, it is possible to save the medical image in the saving device provided in the endoscope system.

There is provided a processor device comprising an endoscope controller that controls the endoscope device comprising the endoscope. The processor device may comprise a medical image acquisition unit that acquires a medical image, a scene-of-interest recognition unit that recognizes a scene of interest from the medical image acquired using the medical image acquisition unit, a degree-of-similarity calculation unit that, for the scene of interest recognized using the scene-of-interest recognition unit, calculates a degree of similarity between the medical image acquired using the medical image acquisition unit and a standard image determined for the scene of interest, and a saving processing unit that performs processing for saving the medical image in a saving device based on the degree of similarity calculated using the degree-of-similarity calculation unit.

According to a sixteenth aspect, there is provided an image processing method comprising a medical image acquisition step of acquiring a medical image, a scene-of-interest recognition step of recognizing a scene of interest from the medical image acquired in the medical image acquisition step, a degree-of-similarity calculation step of, for the scene of interest recognized in the scene-of-interest recognition step, calculating a degree of similarity between the medical image acquired in the medical image acquisition step and a standard image determined for the scene of interest, and a saving processing step of saving the medical image in a saving device based on the degree of similarity calculated in the degree-of-similarity calculation step.

According to the sixteenth aspect, it is possible to obtain the same effects as in the first aspect.

In the sixteenth aspect, the same matters as the matters specified in the second aspect to the thirteenth aspect can be combined as appropriate. In this case, the components that perform processing or functions specified in the image processing device can be ascertained as the components of the image processing method that performs corresponding processing or functions.

According to a seventeenth aspect, there is provided a program that causes a computer to implement a medical image acquisition function of acquiring a medical image, a scene-of-interest recognition function of recognizing a scene of interest from the medical image acquired using the medical image acquisition function, a degree-of-similarity calculation function of, for a scene of interest recognized using the scene-of-interest recognition function, calculating a degree of similarity between the medical image acquired using the medical image acquisition function and a standard image determined for the scene of interest, and a saving processing function of saving the medical image in a saving device based on the degree of similarity calculated using the degree-of-similarity calculation function.

According to the seventeenth aspect, it is possible to obtain the same effects as in the first aspect.

In the seventeenth aspect, the same matters as the matters specified in the second aspect to the thirteenth aspect can be combined as appropriate. In this case, the components that perform processing or functions specified in the image processing device can be ascertained as the components of the program that performs corresponding processing or functions.

The seventeenth aspect can be configured as a system that has at least one or more processors and at least one or more memories, and implements a medical image acquisition function of acquiring a medical image, a scene-of-interest recognition function of recognizing a scene of interest from the medical image acquired using the medical image acquisition function, a degree-of-similarity calculation function of, for a scene of interest recognized using the scene-of-interest recognition function, calculating a degree of similarity between the medical image acquired using the medical image acquisition function and a standard image determined for the scene of interest, and a saving processing function of saving the medical image in the memory based on the degree of similarity calculated using the degree-of-similarity calculation function.

According to the invention, the medical image where the scene of interest is recognized is acquired and saved according to the degree of similarity with the standard image. With this, it is possible to automatically differentiate the medical image where the scene of interest is recognized and to save the medical image according to a differentiation result.

DESCRIPTION OF THE PREFERRED EMBODIMENTS

Figure 1:
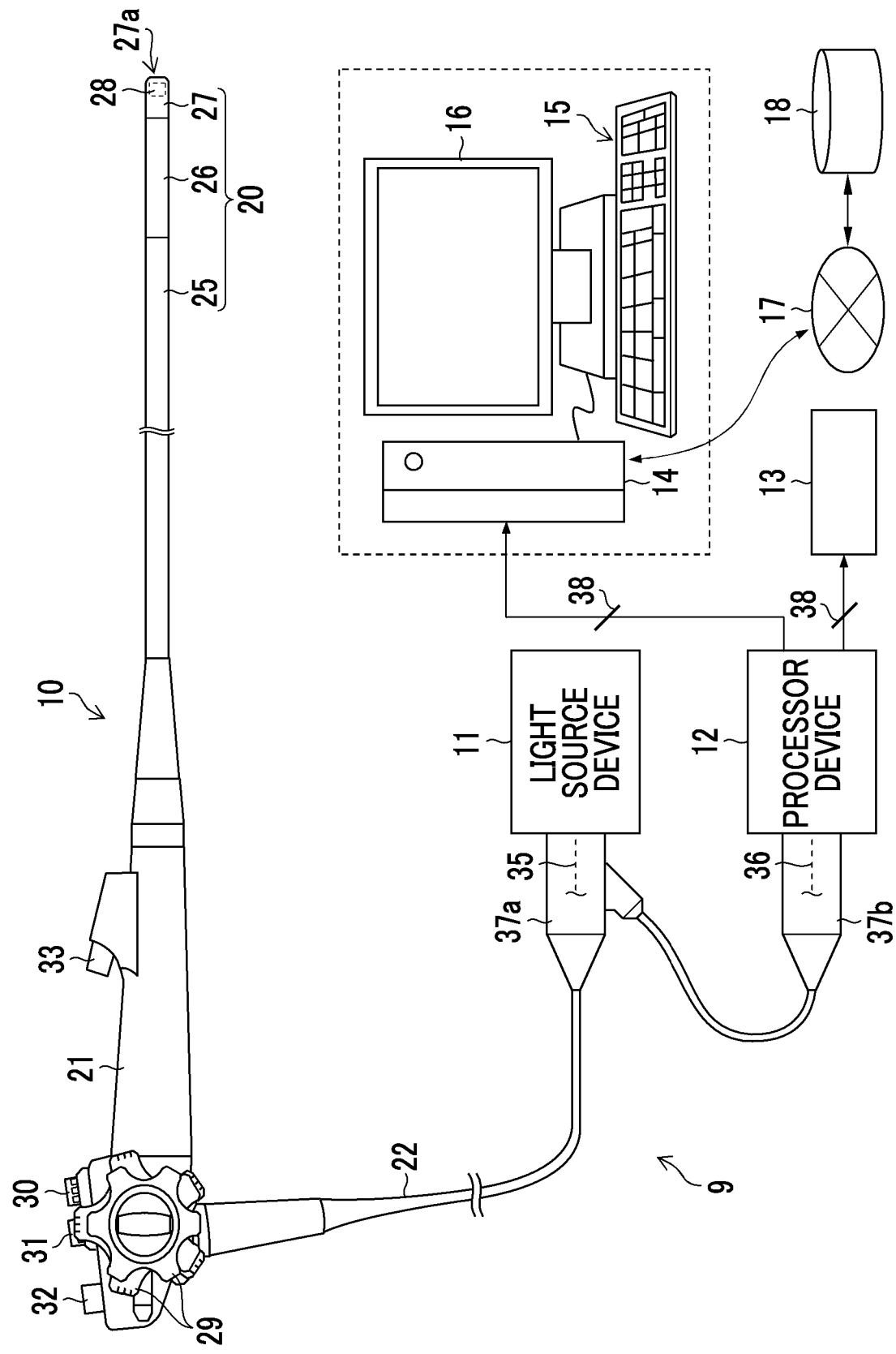
FIG. 1 is a schematic view showing the overall configuration of an endoscope system.

Preferred embodiments of the invention will be described below in detail referring to the accompanying drawings. In the specification, the same components are represented by the same reference numerals, and overlapping description will not be repeated.

[Overall Configuration of Endoscope System]

FIG. 1 is a schematic view showing the overall configuration of an endoscope system. An endoscope system 9 shown in FIG. 1 comprises an endoscope 10, a light source device 11, a processor device 12, a display device 13, an image processing device 14, an input device 15, and a monitor device 16. The endoscope system 9 is connected to a storage device 18 through a network 17 so as to perform communication.

The endoscope 10 is an electronic endoscope. Furthermore, the endoscope 10 is a flexible endoscope. The endoscope 10 comprises an insertion part 20, an operating part 21, and a universal cord 22. The insertion part 20 is inserted into a subject. The insertion part 20 is formed in a small-diameter long shape as a whole.

The insertion part 20 comprises a flexible part 25, a bending part 26, and a distal end part 27. The insertion part 20 is configured by consecutively connecting the flexible part 25, the bending part 26, and the distal end part 27. The flexible part 25 has flexibility in order from a base end side to a distal end side of the insertion part 20. The bending part 26 has a structure capable of being bent in a case where the operating part 21 is operated. The distal end part 27 is embedded with an imaging optical system (not shown), an imaging element 28, and the like.

The imaging element 28 is a CMOS type imaging element or a CCD type imaging element. CMOS is an abbreviation of Complementary Metal Oxide Semiconductor. CCD is an abbreviation of Charge Coupled Device.

In a distal end surface 27a of the distal end part 27, an observation window (not shown) is disposed. The observation window is an opening that is formed in the distal end surface 27a of the distal end part 27. The imaging optical system (not shown) is disposed behind the observation window. Reflected light of a part to be observed is incident on an imaging surface of the imaging element 28 through the observation window, the imaging optical system, and the like. The imaging element 28 images reflected light of the part to be observed incident on the imaging surface of the imaging element 28 and outputs an imaging signal. Imaging stated herein includes a meaning that reflected light from the part to be observed is converted into an electric signal.

The operating part 21 is consecutively connected to the base end side of the insertion part 20. The operating part 21 comprises various operation members that are operated by the practitioner. Specifically, the operating part 21 comprises two kinds of bending operation knobs 29. The bending operation knobs 29 are used in a bending operation of the bending part 26. The practitioner may be referred to as a physician, an operator, a user, or the like.

The operating part 21 comprise an air supply and water supply button 30 and a suction button 31. The air supply and water supply button 30 is used when the practitioner performs an air supply and water supply operation. The suction button 31 is used when the practitioner performs a suction operation.

The operating part 21 comprises a static image capturing instruction unit 32 and a treatment tool inlet 33. The static image capturing instruction unit 32 is operated by the practitioner in capturing a static image of the part to be observed. The treatment tool inlet 33 is an opening through which a treatment tool is inserted into a treatment tool insertion path inserted into the insertion part 20. The treatment tool insertion path and the treatment tool are not shown. The static image is represented by reference numeral 38c and is displayed in FIG. 3.

The universal cord 22 is a connection cord that connects the endoscope 10 to the light source device 11. The universal cord 22 includes a light guide 35, a signal cable 36, and a fluid tube (not shown) inserted into the insertion part 20.

A distal end part of the universal cord 22 comprises a connector 37a that is connected to the light source device 11, and a connector 37b that is branched from the connector 37a and is connected to the processor device 12.

In a case where the connector 37a is connected to the light source device 11, the light guide 35 and the fluid tube (not shown) are inserted into the light source device 11. With this, necessary illumination light, water, and air are supplied from the light source device 11 to the endoscope 10 through the light guide 35 and the fluid tube (not shown).

As a result, illumination light is irradiated from an illumination window (not shown) in the distal end surface 27a of the distal end part 27 toward the part to be observed. Furthermore, air or water is injected from an air supply and water supply nozzle (not shown) in the distal end surface 27a of the distal end part 27 according to a press operation of the air supply and water supply button 30.

In a case where the connector 37b is connected to the processor device 12, the signal cable 36 and the processor device 12 are electrically connected. With this, the imaging signal of the part to be observed is output from the imaging element 28 of the endoscope 10 to the processor device 12 through the signal cable 36, and a control signal is output from the processor device 12 to the endoscope 10.

In the embodiment, although a case where the flexible endoscope is exemplified as the endoscope 10 has been described, various electronic endoscopes that can image video of the part to be observed, such as a rigid endoscope, may be used as the endoscope 10.

The light source device 11 supplies illumination light to the light guide 35 of the endoscope 10 through the connector 37a. As illumination light, white light or light in a specific wavelength range can be applied. As illumination light, white light and light in a specific wavelength range may be combined. The light source device 11 is configured to select light in a wavelength range according to an observation purpose as illumination light as appropriate.

White light may be light in a white wavelength range or light in a plurality of wavelength ranges. The specific wavelength range is a range narrower than the white wavelength range. As light in the specific wavelength range, light in one kind of wavelength range may be applied or light in a plurality of wavelength ranges may be applied. The specific wavelength range may be referred to as special light.

The processor device 12 controls the operation of the endoscope 10 through the connector 37b and the signal cable 36. Furthermore, the processor device 12 acquires the imaging signal from the imaging element 28 of the endoscope 10 through the connector 37b and the signal cable 36. The processor device 12 acquires the imaging signal output from the endoscope 10 by applying a prescribed frame rate.

The processor device 12 generates an endoscope image 38, which is an observation image of the part to be observed, based on the imaging signal acquired from the endoscope 10. The endoscope image 38 stated herein includes video. The endoscope image 38 may include a static image. Video is represented by reference numeral 38a and is displayed in FIG. 3.

The processor device 12 generates a static image of the part to be observed based on the imaging signal acquired from the imaging element 28 in parallel with generation of video in a case where the static image capturing instruction unit 32 of the operating part 21 is operated. The static image may be generated with high resolution with respect to resolution of video.

In generating the endoscope image 38, the processor device 12 performs correction of image quality, to which digital signal processing, such as white balance adjustment and shading correction, is applied. The processor device 12 may add accessory information prescribed by the DICOM standard to the endoscope image 38. DICOM is an abbreviation of Digital Imaging and Communications in Medicine.

The endoscope image 38 is an in-vivo image obtained by imaging the inside of the subject, that is, the inside of a living body. In a case where the endoscope image 38 is an image obtained through imaging using light in a specific wavelength range, both images are special light images. Then, the processor device 12 outputs the generated endoscope image 38 to the display device 13 and the image processing device 14. The processor device 12 may output the endoscope image 38 to the storage device 18 through the network 17 according to a communication protocol conforming to the DICOM standard.

The display device 13 is connected to the processor device 12. The display device 13 displays the endoscope image 38 transmitted from the processor device 12. The practitioner can perform an operation to move the insertion part 20 forward and backward while confirming the endoscope image 38 displayed on the display device 13. The practitioner can operate the static image capturing instruction unit 32 to capture the static image of the part to be observed in a case where a lesion or the like is detected in the part to be observed.

As the image processing device 14, a computer is used. As the input device 15, a keyboard, a mouse, or the like that can be connected to the computer are used. The connection of the input device 15 and the computer may be either of wired connection or wireless connection. As the monitor device 16, various monitors that can be connected to the computer are used.

As the image processing device 14, a diagnosis support device, such as a workstation or a server device, may be used. In this case, the input device 15 and the monitor device 16 are provided in each of a plurality of terminals connected to a workstation or the like. In addition, as the image processing device 14, a clinical service support device that supports creation of a medical report or the like may be used.

The image processing device 14 performs acquisition of the endoscope image 38 and storage of the endoscope image 38. The image processing device 14 performs playback control of the monitor device 16. That is, the image processing device 14 comprises an endoscope image acquisition unit that acquires the endoscope image 38, an image storage unit that stores the endoscope image 38, and a display controller that performs display control of the endoscope image 38.

Figure 3:
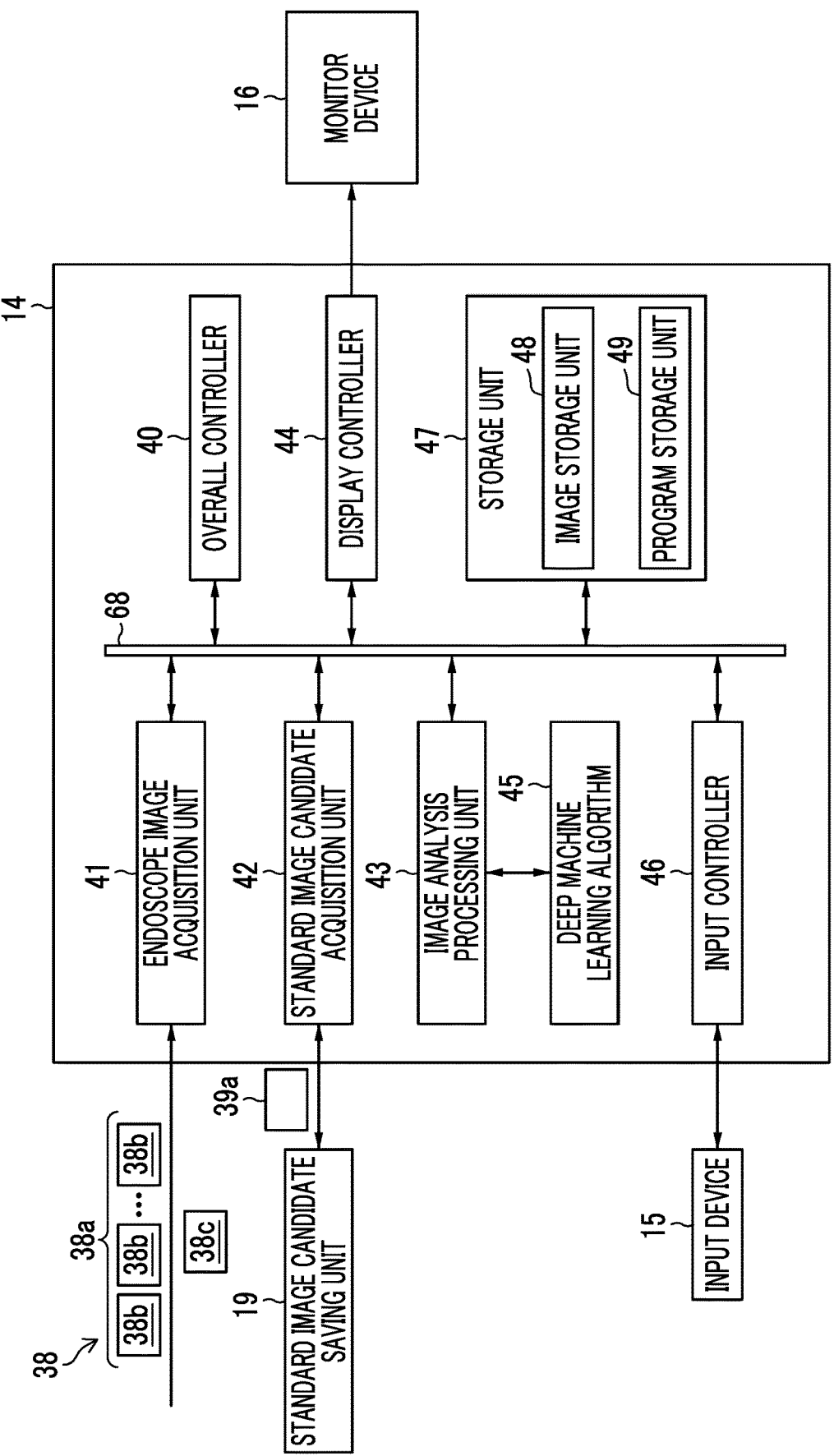
FIG. 3 is a functional block diagram showing functions of an image processing device according to a first embodiment.

The endoscope image acquisition unit is represented by reference numeral 41 and is displayed in FIG. 3. The image storage unit is represented by reference numeral 48 and is displayed in FIG. 3. The display controller is represented by reference numeral 44 and is displayed in FIG. 3. In the specification, image storage can be replaced with image saving. Image storage stated herein means non-transitory image storage. The image processing device 14 may comprise a memory for primary storage that primarily stores an image.

The input device 15 is used for an input an operation instruction to the image processing device 14. The monitor device 16 performs the display of the endoscope image 38 under the control of the image processing device 14. The monitor device 16 may function as a display unit of various kinds of information in the image processing device 14.

The image processing device 14 is connected to the storage device 18 through the network 17. For a storage format of an image and communication between the devices by way of the network 17, the DICOM standard, a protocol conforming to the DICOM standard, and the like can be applied.

The term "image" described above includes a meaning of image data representing an image. The term "image" stated in the specification means at least one of an image itself or an image data.

As the storage device 18, a storage that stores data in a non-transitory manner, or the like can be applied. The storage device 18 may be managed using a server device (not shown). As the server device, a computer that stores and manages various kinds of data can be applied.

The endoscope system 9 shown in FIG. 1 is an example of an endoscope device that comprises an endoscope. A system including the endoscope system 9 shown in FIG. 1 and the image processing device 14 is an example of an endoscope system comprising an endoscope device that comprises an endoscope, and an image processing device.

[Configuration of Image Processing Device According to First Embodiment]

Next, an image processing device according to a first embodiment will be described.

[Description of Problem]

The endoscope system 9 shown in FIG. 1 displays, on the display device 13, an endoscope image 38 obtained by imaging a body cavity using the imaging element 28 provided in the distal end part 27 of the endoscope 10. The practitioner can perform inspection, treatment, and the like while confirming the image displayed on the display device 13. In an endoscopy using the endoscope system 9, the imaging element 28 provided in the distal end part 27 of the endoscope 10 is inserted into a body of a patient. The practitioner can operate the endoscope 10 and can observe an image inside the body cavity displayed on the display device 13.

Furthermore, the practitioner can perform water supply to perform cleaning inside the body. In a case where a part practitioner finds a part suspected to be a lesion from the image inside the body cavity, the practitioner can perform dispersion of indigo, observation of the part suspected to be a lesion on a magnified scale, and a biopsy on the part suspected to be a lesion.

In this way, in the endoscopy, since it is necessary to observe the image inside the body cavity while performing various practices, oversight of the part suspected to be a lesion may occur.

Accordingly, as support for suppressing oversight of the part suspected to be a lesion, automatic recognition of the part suspected to be a lesion, to which a recognizer learned using machine learning is applied, is exemplified. For example, a recognizer learned using machine learning is applied during an endoscopy to automatically recognize the part suspected to be a lesion. In a case where the part suspected to be a lesion is recognized, a frame surrounding the part suspected to be a lesion displayed on the display device 13 is displayed on the display device 13. With this, notification is given that the part suspected to be a lesion is found, and it is possible to suppress oversight of the practitioner of the part suspected to be a lesion.

However, in a case where machine learning is insufficient, there may be an image that is hardly recognized by the recognizer. Examples of a case where an image is hardly recognized include a case where a scene of interest cannot be recognized, a case where a scene of interest is recognized, but a score of a likelihood of the scene of interest is smaller than a prescribed criterion, a case where a scene of interest is recognized, but reliability is low, a case where misdetection occurs more than a criterion, and the like.

In a case where there is an image that is hardly recognized, the recognizer using machine learning, such as deep learning, needs to collect images that are hardly recognized by the recognizer, and perform new learning using the collected images. On the other hand, the images that are hardly recognized by the recognizer are hardly collected. To begin with, an image that is hardly recognized by the recognizer cannot be distinguished from an image that is not recognized as a scene of interest. The same applies to the score representing the likelihood of the scene of interest and reliability.

The image processing device and method according to the first embodiment described below can differentiate and collect images that are hardly recognized by the recognizer, and can enable support for an endoscopy. Furthermore, it is possible to perform machine learning using the collected images and to achieve performance improvement of the recognizer.

[Outline]

The image processing device and method according to the embodiment select an image representing a scene hardly recognized by the recognizer as a standard image. In a case where the degree of similarity between the endoscope image and the standard image is equal to or greater than a prescribed threshold value, the endoscope image is saved as an image hardly recognized by the recognizer. That is, the image processing device and method according to the embodiment differentiate an image similar to the scene hardly recognized by the recognizer and saves the image according to a differentiation result.

The term "scene" stated in the specification can both of a case where a scene is composed using one image or a case where a scene is composed using an image group including a plurality of images. In the embodiment, a case where the scene of interest is composed using one frame image 38b or one static image is illustrated. The same applies to a second embodiment.

[Hardware Configuration]

Figure 2:
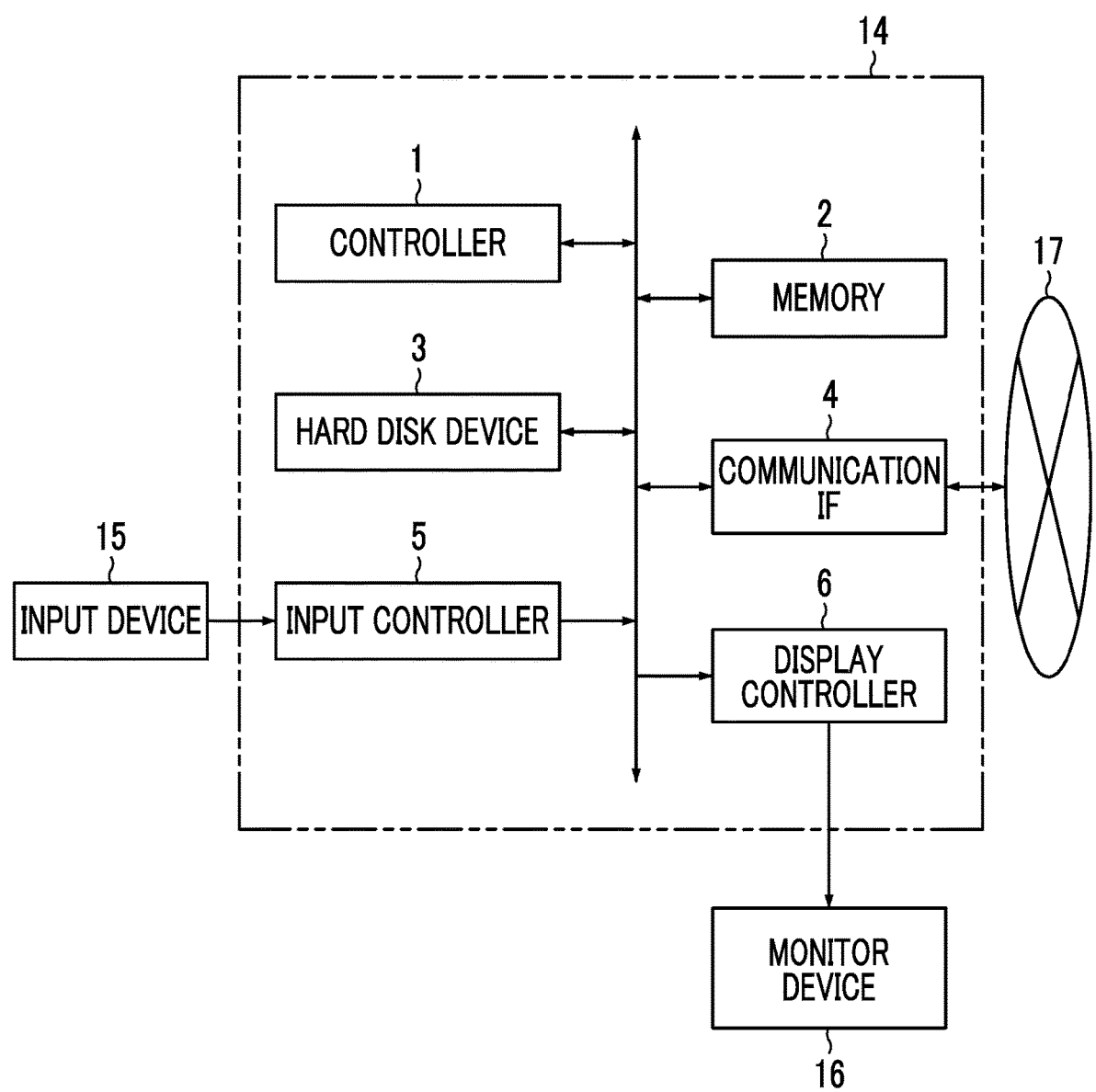
FIG. 2 is a block diagram showing a configuration example of hardware of an image processing device.

FIG. 2 is a block diagram showing a configuration example of hardware of the image processing device. The image processing device 14 comprises a controller 1, a memory 2, a hard disk device 3, a communication interface 4, an input controller 5, and a display controller 6.

<Controller>

The controller 1 functions as an overall controller, various arithmetic units, and a storage controller of the image processing device 14. The controller 1 executes a program stored in a read only memory (ROM) provided in the memory 2. The controller 1 may download a program from an external storage device through the communication interface 4 and may execute the downloaded program. The external storage device may be connected to the image processing device 14 through the network 17 so as to perform communication.

The controller 1 executes various kinds of processing in cooperation with various programs with a random access memory (RAM) provided in the memory 2 as an arithmetic operation area. With this, various functions of the image processing device 14 are implemented.

The controller 1 controls reading of data from the hard disk device 3 and writing of data to the hard disk device 3. The controller 1 may include one or two or more processors.

Examples of the processor include a field programmable gate array (FPGA), a programmable logic device (PLD), or the like is exemplified. A circuit configuration of the FPGA and the PLD can be changed after manufacturing.

Another example of the processor is an application specific integrated circuit (ASIC). The ASIC includes a dedicated circuit configuration that is designed in order to execute specific processing.

As the controller 1, two or more processors of the same kind can be applied. For example, the controller 1 may use two or more FPGAs or two PLDs. As the controller 1, two or more processors of different kinds may be applied. For example, one or more FPGAs and one or more ASICs may be applied as the controller 1.

In a case where a plurality of controllers are provided, a plurality of controllers may be configured using one processor. An example where a plurality of controllers are configured of one processor is a form in which one processor is configured using a combination of one or more central processing units (CPUs) and software, and the processor functions as a plurality of controllers. A graphics processing unit (GPU) that is a processor specialized in image processing may be applied instead of the CPU or in addition to the CPU. The term "software" stated herein is synonymous with a program. A representative example where a plurality of controllers are configured using one processor is a computer, such as a client device or a server device.

Another example where a plurality of controllers are configured of one processor is a form in which a processor that implements the functions of the entire system including a plurality of controllers with one IC chip is used. A representative example of the processor that implements the functions of the entire system including a plurality of controllers with one IC chip is System On Chip (SoC). IC is an abbreviation of Integrated Circuit.

In this way, the controller 1 is configured using one or more of various processors as a hardware structure.

<Memory>

The memory 2 comprises a ROM (not shown) and a RAM (not shown). The ROM stores various programs that are executed in the image processing device 14. The ROM stores parameters, files, and the like that are used to execute various programs. The RAM functions a temporary storage area of data, a work area of the controller 1, and the like.

<Hard Disk Device>

The hard disk device 3 stores various kinds of data in a non-transitory manner. Specifically, the hard disk device 3 stores an observation image of the endoscope 10, a medical image acquired from the external storage device, such as the storage device 18 shown in FIG. 1, and the like. The hard disk device 3 may be attached to the outside of the image processing device 14. A large-capacity semiconductor memory device may be applied instead of or in addition to the hard disk device 3.

<Communication Interface>

The communication interface 4 performs data communication with external devices, such as the storage device 18 shown in FIG. 1. IF shown in FIG. 2 is an abbreviation of interface.

<Input Controller>

The input controller 5 an interface that receives a signal transmitted from the input device 15, such as a keyboard or a mouse, and converts the signal into a signal in a format that is applied to the image processing device 14.

<Display Controller>

The display controller 6 is an interface that converts a signal representing an image generated in the image processing device 14 into a video signal that is displayed using the monitor device 16. The display controller 6 transmits the video signal representing the image to the monitor device 16.

The hardware configuration of the image processing device 14 shown in FIG. 2 is an example, and components can be added, deleted, and changed as appropriate.

[Functions of Image Processing Device According to First Embodiment]

FIG. 3 is a functional block diagram showing the functions of the image processing device according to the first embodiment. The image processing device 14 shown in FIG. 3 comprises an overall controller 40, an endoscope image acquisition unit 41, a standard image candidate acquisition unit 42, an image analysis processing unit 43, a display controller 44, an input controller 46, and a storage unit 47.

The overall controller 40, the endoscope image acquisition unit 41, the standard image candidate acquisition unit 42, the image analysis processing unit 43, the display controller 44, the input controller 46, and the storage unit 47 are connected through a communication signal line 68 so as to perform communication with one another. Each unit will be described below in detail.

<Overall Controller>

The overall controller 40 integrally controls the endoscope image acquisition unit 41, the standard image candidate acquisition unit 42, the image analysis processing unit 43, and the display controller 44 based on execution of a control program of the image processing device 14.

<Endoscope Image Acquisition Unit>

The endoscope image acquisition unit 41 acquires the endoscope image 38 generated using the processor device 12 shown in FIG. 1. The endoscope image acquisition unit 41 may acquire an endoscope image stored in the external storage device and captured using the endoscope device. The endoscope image acquisition unit 41 may acquire the endoscope image 38 through various information storage mediums, such as a memory card.

The endoscope image acquisition unit 41 acquires video 38a. The endoscope image acquisition unit 41 may acquire time-series frame images 38b as the video 38a. The endoscope image acquisition unit 41 may acquire a static image 38c. In a case where an imaging operation of the static image 38c is performed in the middle of imaging of the video 38a, the endoscope image acquisition unit 41 acquires the static image 38c from the processor device 12 shown in FIG. 1. The endoscope image acquisition unit 41 is an example of a medical image acquisition unit that acquires a medical image.

<Standard Image Candidate Acquisition Unit>

The standard image candidate acquisition unit 42 acquires a standard image candidate 39a to be a candidate of a standard image from among medical images that are managed using a database management system or the like. The standard image is represented by reference numeral 39 and is displayed in FIG. 4. The standard image candidate acquisition unit 42 acquires the standard image candidate 39a from an external standard image candidate saving unit 19 of the image processing device 14. An example of the standard image candidate saving unit 19 is a storage device, such as a storage including the storage device 18 shown in FIG. 1.

The standard image candidate acquisition unit 42 is an example of a component of a standard image acquisition unit that acquires a standard image. The standard image candidate saving unit 19 is an example of a medical image saving device in which a plurality of medical images acquired in advance are saved.

<Image Analysis Processing Unit>

The image analysis processing unit 43 executes analysis processing of the endoscope image 38 acquired using the endoscope image acquisition unit 41 through deep machine learning based on a deep machine learning algorithm 45. Details of the analysis processing of the endoscope image 38 will be described below.

The deep machine learning algorithm 45 is an algorithm including a known convolutional neural network method, a fully connected layer, and an output layer. Deep machine learning may be referred to as deep learning.

A convolutional neural network is repetition processing of a convolution layer and a pooling layer. The convolutional neural network may be referred to as a convolution neural network. Image analysis processing using deep machine learning is a known technique, and thus, specific description will not be repeated. Deep machine learning is an example of machine learning.

<Display Controller>

The display controller 44 functions as a display driver that controls image display in playing back the endoscope image 38 using the monitor device 16. The display controller 44 may display the static image 38c captured during playback of the video 38a on the video 38a in a superimposed manner using the monitor device 16. The display controller 44 may display text information or the like on the video 38a during playback or the static image 38c in a superimposed manner using the monitor device 16.

<Input Controller>

The input controller 46 converts a signal input from the input device 15 into a signal in a format that is applied to the image processing device 14, and transmits the converted signal to the overall controller 40. The overall controller 40 controls each unit of the image processing device 14 based on information input from the input device 15.

<Storage Unit>

The storage unit 47 comprises an image storage unit 48 and a program storage unit 49. The image storage unit 48 stores the endoscope image 38 acquired using the endoscope image acquisition unit 41. The image stored in the image storage unit 48 is read to the image analysis processing unit 43 under the control of the overall controller 40.

The program storage unit 49 stores various programs that operate the image processing device 14. Various programs stored in the program storage unit 49 are read to each unit under the control of the overall controller 40. The image storage unit 48 is an example of a saving device that saves a medical image.

[Configuration Example of Image Analysis Processing Unit]

Figure 4:
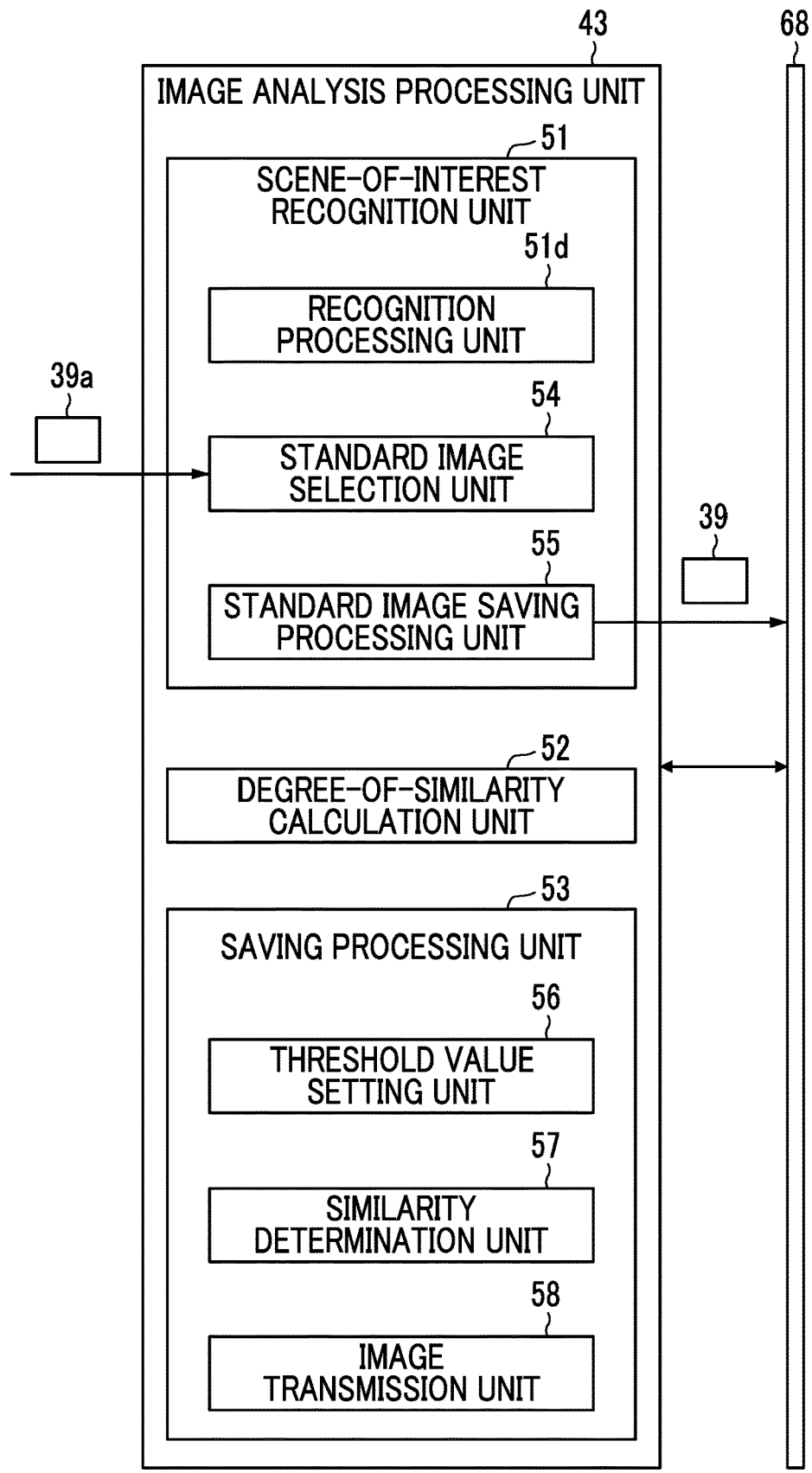
FIG. 4 is a functional block diagram showing functions of an image analysis processing unit shown in FIG. 3.

FIG. 4 is a functional block diagram showing the functions of the image analysis processing unit shown in FIG. 3. The image analysis processing unit 43 comprises a scene-of-interest recognition unit 51, a degree-of-similarity calculation unit 52, and a saving processing unit 53. Each unit will be described below in detail.

<Scene-of-Interest Recognition Unit>

The scene-of-interest recognition unit 51 comprises a recognition processing unit 51d, a standard image selection unit 54, and a standard image saving processing unit 55. The recognition processing unit 51d functions as a recognizer that recognizes a scene of interest. The recognition processing unit 51d performs recognition of a feature of a prescribed scene of interest for the standard image candidate 39a acquired through the standard image candidate acquisition unit 42 shown in FIG. 3. The feature of the prescribed scene of interest may be automatically set or may be manually set.

The standard image selection unit 54 selects a standard image 39, which is hardly recognized by the scene-of-interest recognition unit 51, from among the standard image candidates 39a unrecognizable as a scene of interest by the recognition processing unit 51d. The standard image candidate 39a is an example of a medical image that is unrecognized as a scene of interest by the scene-of-interest recognition unit.

The standard image selection unit 54 may select the standard image 39 based on a manually input selection signal or may prepare a correct answer image in advance, may compare the correct answer image with a recognition result of the recognition processing unit 51d, and may automatically select the standard image 39 using a comparison result. In a case where there are two or more kinds of scenes that are hardly recognized by the scene-of-interest recognition unit 51, the standard image selection unit 54 may select the standard image 39 for each scene. The standard image selection unit 54 is an example of a component of a standard image acquisition unit that acquires a standard image.

The standard image saving processing unit 55 executes processing for saving the selected standard image 39. The standard image 39 is saved using the image storage unit 48 shown in FIG. 3. In a case where there are two or more kinds of scenes that are hardly recognized by the scene-of-interest recognition unit 51, the scene and the standard image 39 are saved in association with each other.

The standard image 39 may be saved in an external storage device of the image processing device 14. An example of the external storage device is the storage device 18 shown in FIG. 1. The standard image 39 may be read from the external storage device of the image processing device 14 through a network. An example of the network is the network 17 shown in FIG. 1.

A feature quantity may be extracted from the standard image 39, and the feature quantity of the standard image 39 may be saved. In extracting the feature quantity, a known technique can be applied.

<Degree-of-Similarity Calculation Unit>

The degree-of-similarity calculation unit 52 calculates the degree of similarity between the endoscope image 38 and the standard image 39. The degree-of-similarity calculation unit 52 may calculate the degree of similarity from the endoscope image 38 itself and the standard image 39 itself. The degree-of-similarity calculation unit 52 may extract the feature quantities of the endoscope image 38 and the standard image 39 and may calculate the degree of similarity between the endoscope image 38 and the standard image 39 based on the feature quantities. The degree-of-similarity calculation unit 52 may calculate a value greater than 0 and equal to or less than 1 as the degree of similarity. A relatively large degree of similarity represents that the endoscope image 38 and the standard image 39 are similar. A relatively small degree of similarity represents that the endoscope image 38 and the standard image 39 are not similar.

The degree-of-similarity calculation unit 52 is an example of a medical image feature quantity extraction unit that extracts a feature quantity from a medical image and an example of a standard image feature quantity extraction unit that extracts a feature quantity from a standard image. The degree-of-similarity calculation unit 52 is an example of a standard image feature quantity acquisition unit that acquires a feature quantity of a standard image.

<<Specific Example of Calculation of Degree of Similarity>>

It is assumed that the number of pixels of the endoscope image 38 and the number of pixels of the standard image 39 are m×n pixels. m and n are an arbitrary integer equal to or greater than 1. m and n can be the same value. A pixel value of an i-th pixel of the endoscope image 38 is $g_{1i}$. A pixel value of an i-th pixel of the standard image 39 is $g_{2i}$. An arbitrary constant is c. The constant c is a maximum value of a value that can be taken as a pixel value. The degree of similarity between the endoscope image 38 and the standard image 39 is D. D is represented using Expression 1.

$$D = c - \Sigma(g_{1i} - g_{2i})^2 \qquad \text{Expression 1}$$

That is, the pixel values of all pixels are obtained for the endoscope image 38 and the standard image 39. For all pixels of both images, a difference between the pixel values of the pixels is obtained. Each obtained difference value is squared and totalized to calculate a difference square sum. Then, a value obtained by subtracting the difference square sum from the constant can be applied as the degree of similarity D between the endoscope image 38 and the standard image 39. The degree of similarity D may be set to a value greater than 0 and equal to or less than 1.0 through division using the constant c.

Another specific example of calculation of the degree of similarity is a method using a convolutional neural network. The degree of similarity D between the endoscope image 38 and the standard image 39 is represented using Expression 2.

$$D = \sqrt{\Sigma(h_{1,j} - h_{2,j})^2} \qquad \text{Expression 2}$$

$$\text{where, } 1 = \sqrt{\Sigma(h_{1,j})^2}$$

$$1 = \sqrt{\Sigma(h_{2,j})^2}$$

In Expression 2, $h_{1j}$ represents a feature quantity of a j-th pixel of the endoscope image 38. In Expression 2, $h_{2j}$ represents a feature quantity of a j-th pixel of the standard image. The feature quantity $h_{1j}$ and the feature quantity $h_{2j}$ are an output of the convolutional neural network learned the degree of similarity.

The feature quantity $h_{1j}$ of the j-th pixel of the endoscope image 38 in Expression 2 is represented using Expression 3. Similarly, the feature quantity $h_{2j}$ of the j-th pixel of the standard image 39 in Expression 2 is represented using Expression 4.

$$(h_{1,1} \ldots h_{1,J}) = f\left(\begin{pmatrix} g_{1,1} & \cdots & g_{1,m} \\ & \ddots & \\ g_{1,(nm-n)} & & g_{1,nm} \end{pmatrix}\right) \quad \text{Expression 3}$$

$$(h_{2,1} \ldots h_{2,J}) = f\left(\begin{pmatrix} g_{2,1} & \cdots & g_{2,m} \\ & \ddots & \\ g_{2,(nm-n)} & & g_{2,nm} \end{pmatrix}\right) \quad \text{Expression 4}$$

In Expressions 3 and 4, f represents the convolutional neural network. In Expression 3, $g_{1j}$ is the pixel value of the j-th pixel of the endoscope image 38. In Expression 4, $g_{2j}$ is the pixel value of the j-th pixel of the standard image 39. The number of pixels of the endoscope image 38 and the number of pixels of the standard image 39 are m×n pixels, and m and n are an arbitrary integer equal to or greater than 1. m and n can be the same value. Normally, j is a value smaller than the number of pixels.

The degree of similarity between the endoscope image 38 and the standard image 39 is not limited to the above-described example. The degree of similarity between the endoscope image 38 and the standard image 39 may be derived using other methods.

<Saving Processing Unit>

The saving processing unit 53 comprises a threshold value setting unit 56, a similarity determination unit 57, and an image transmission unit 58. The threshold value setting unit 56 sets a threshold value that is used in determining whether or not the endoscope image 38 and the standard image 39 are similar. The threshold value setting unit 56 can set a threshold value based on an input signal input from the input device 15 shown in FIG. 3. The threshold value setting unit 56 may set a fixed threshold value.

The threshold value is determined according to a numerical value range of the degree of similarity. In a case where the degree of similarity is calculated as a value greater than 0 and equal to or less than 1.0, the threshold value can be set to a value greater than 0 and equal to or less than 1.0. An example of the threshold value is 0.5. Another example of the threshold value is a value equal to or greater than 0.1 and equal to or less than 0.5.

The similarity determination unit 57 classifies the endoscope image 38 as a target to be saved in a case where the degree of similarity between the endoscope image 38 and the standard image 39 is equal to or greater than the threshold value. The similarity determination unit 57 classifies the endoscope image 38 as a target to be not saved in a case where the degree of similarity between the endoscope image 38 and the standard image 39 is less than the threshold value. That is, the similarity determination unit 57 classifies the endoscope image 38 similar to the standard image 39 as a target to be saved.

The similarity determination unit 57 may classify the endoscope image 38, for which similarity determination is performed, into a target to be saved as the video 38a or may classify the endoscope image 38 into a target to be saved as the static image 38c. The similarity determination unit 57 may classify several frames before and after the frame image 38b, for which similarity determination is performed, in the video 38a into a target to be saved.

In a case where the endoscope image 38 is classified into a target to be saved as the static image 38c, the similarity determination unit 57 may classify several static images 38c before and after the static image 38c, for which determination is performed whether or not the static image 38c is similar to the standard image 39, into a target to be saved.

<Image Transmission Unit>

The image transmission unit 58 transmits the endoscope image 38 classified as a target to be saved to the image storage unit 48 shown in FIG. 3. The image transmission unit 58 may transmit the endoscope image 38 classified as a target to be saved to the external storage device of the image processing device 14. The endoscope image 38 classified as a target to be saved may be managed into a database.

<Advantage of Using Degree of Similarity for Classification of Endoscope Image>

It is possible to calculate the degree of similarity between the endoscope image 38 and the standard image 39 regardless of a result of recognition of the scene of interest of the endoscope image 38, and to compare both images. With this, it is possible to collect images that are hardly recognized as a scene of interest.

[Procedure of Image Processing Method According to First Embodiment]

<Overall Flow of Image Processing Method>

Figure 5:
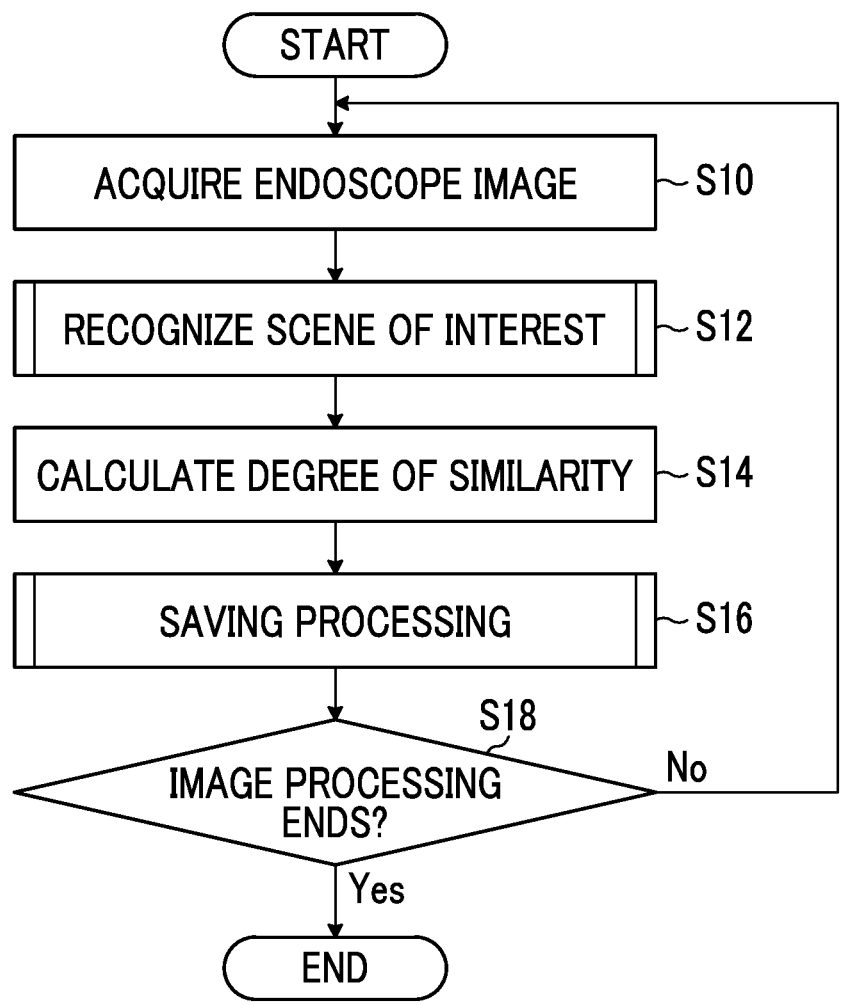
FIG. 5 is a flowchart showing a flow of a procedure of an image processing method according to the first embodiment.

FIG. 5 is a flowchart showing a flow of a procedure of the image processing method according to the first embodiment. In an endoscope image acquisition step S10, the endoscope image acquisition unit 41 shown in FIG. 3 acquires the endoscope image 38 acquired using the endoscope 10 shown in FIG. 1. The procedure progresses to a scene-of-interest recognition step S12 after the endoscope image acquisition step S10. The endoscope image acquisition step S10 is an example of a medical image acquisition step.

In the scene-of-interest recognition step S12, the scene-of-interest recognition unit 51 shown in FIG. 4 acquires the standard image candidates 39a through the standard image candidate acquisition unit 42 and selects the standard image 39 from among the standard image candidates 39a. The standard image 39 is saved in the image storage unit 48.

The procedure progresses to a degree-of-similarity calculation step S14 after the scene-of-interest recognition step S12. The scene-of-interest recognition step S12 may be executed prior to the endoscope image acquisition step S10. The scene-of-interest recognition step S12 may be executed in parallel with the endoscope image acquisition step S10. Details of the scene-of-interest recognition step S12 will be described below.

In the degree-of-similarity calculation step S14, the degree-of-similarity calculation unit 52 calculates the degree of similarity between the endoscope image 38 and the standard image 39. The procedure progresses to a saving processing step S16 after the degree-of-similarity calculation step S14.

In the saving processing step S16, the saving processing unit 53 compares the degree of similarity calculated in the degree-of-similarity calculation step S14 with the prescribed threshold value. In a case where the degree of similarity is equal to or greater than the threshold value, the endoscope image 38 is transmitted to the image storage unit 48. The procedure progresses to an image processing end determination step S18 after the saving processing step S16.

In the image processing end determination step S18, the image processing device 14 determines whether or not to end the image processing. In a case where the image processing method continues, a determination result is No. In a case where the determination result is No, the procedure of the image processing method progresses to the endoscope image acquisition step S10. Hereinafter, the image processing device 14 repeatedly executes the steps of the endoscope image acquisition step S10 to the image processing end determination step S18 until the determination result in the image processing end determination step S18 is Yes.

On the other hand, in the image processing end determination step S18, in a case where the image processing method ends, the determination result is Yes. In a case where a determination result is Yes, the image processing device 14 ends the image processing method.

<Flow of Scene-of-Interest Recognition Step>

Figure 6:
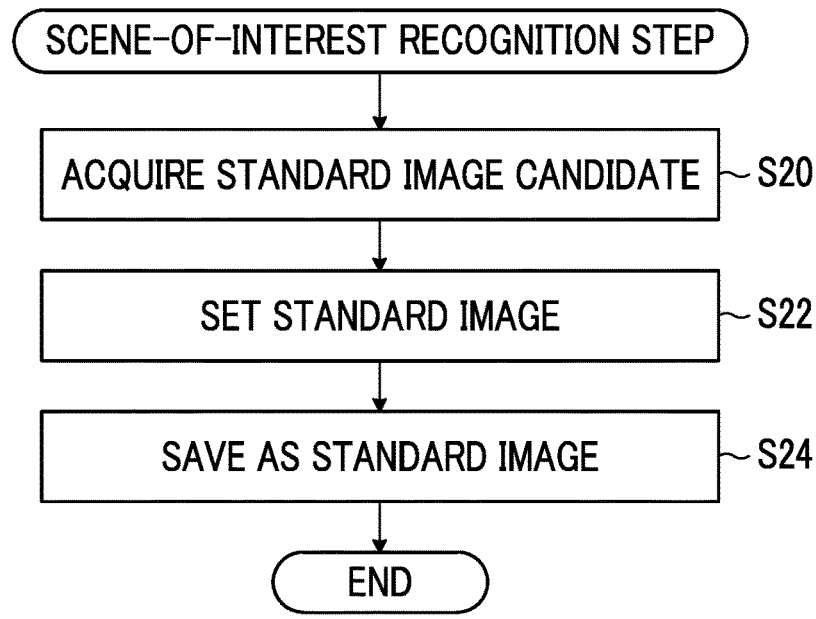
FIG. 6 is a flowchart showing a flow of a procedure of a scene-of-interest recognition step shown in FIG. 5.

FIG. 6 is a flowchart showing a flow of a procedure of the scene-of-interest recognition step shown in FIG. 5. The scene-of-interest recognition step S12 includes a standard image candidate acquisition step S20, a standard image setting step S22, and a standard image saving step S24.

<<Standard Image Candidate Acquisition Step>>

In the standard image candidate acquisition step S20, the scene-of-interest recognition unit 51 shown in FIG. 4 acquires the standard image candidates 39a through the standard image candidate acquisition unit 42. The procedure progresses to the standard image setting step S22 after the standard image candidate acquisition step S20. In the standard image setting step S22, the standard image selection unit 54 performs scene-of-interest recognition of the standard image candidates 39a. The standard image 39 is selected from among the standard image candidates 39a where the scene of interest cannot be recognized. The procedure progresses to the standard image saving step S24 after the standard image setting step S22.

In the standard image saving step S24, the standard image saving processing unit 55 saves the standard image 39 selected in the standard image setting step S22 in the image storage unit 48. After the standard image saving step S24, the scene-of-interest recognition unit 51 ends the scene-of-interest recognition step S12.

<<Saving Processing Step>>

Figure 7:
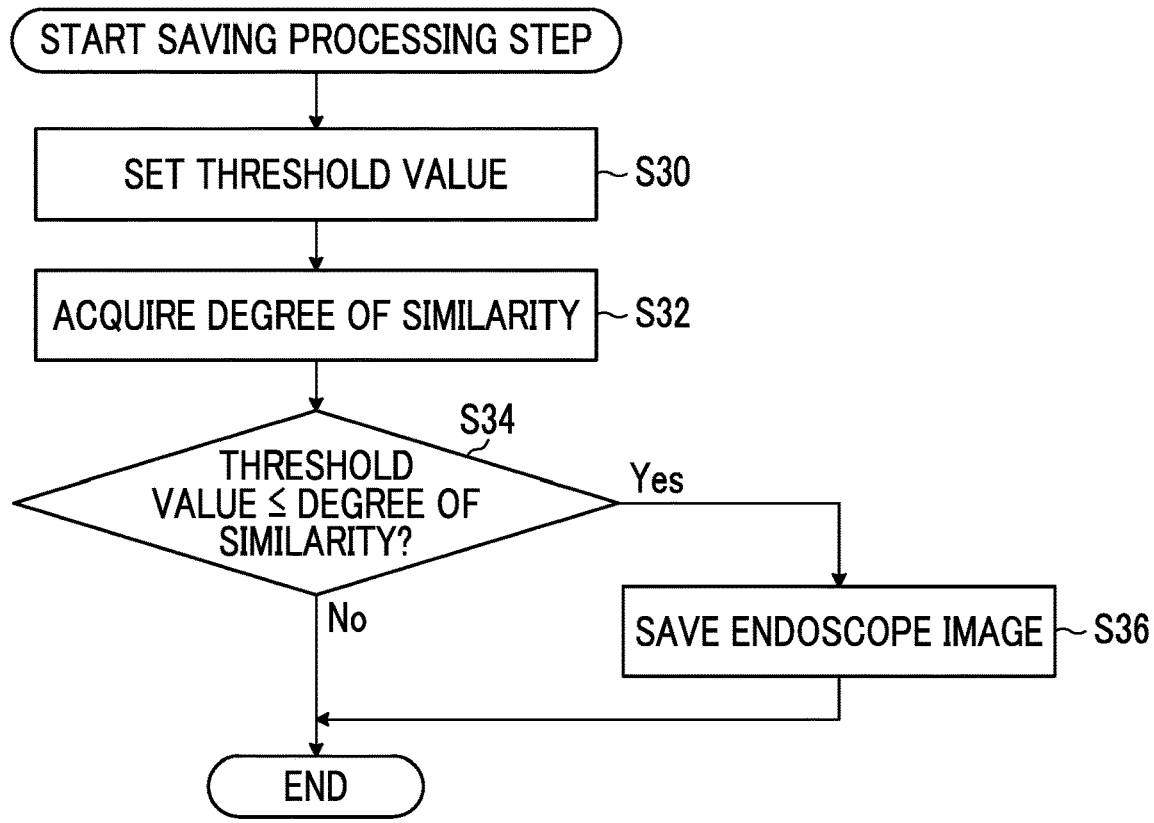
FIG. 7 is a flowchart showing a flow of a procedure of a saving processing step shown in FIG. 5.

FIG. 7 is a flowchart showing a flow of a procedure of the saving processing step shown in FIG. 5. The saving processing step S16 includes a threshold value setting step S30, a degree-of-similarity acquisition step S32, a similarity determination step S34, and an endoscope image saving step S36.

In the threshold value setting step S30, the threshold value setting unit 56 sets the threshold value that is used in determining whether or not the endoscope image 38 and the standard image 39 are similar. The procedure progresses to the degree-of-similarity acquisition step S32 after the threshold value setting step S30.

In the degree-of-similarity acquisition step S32, the similarity determination unit 57 acquires the degree of similarity between the endoscope image 38 and the standard image 39 calculated in the degree-of-similarity calculation step S14 shown in FIG. 5. The procedure progresses to the similarity determination step S34 after the degree-of-similarity acquisition step S32.

In the similarity determination step S34, the similarity determination unit 57 compares the degree of similarity between the endoscope image 38 and the standard image 39 with the threshold value. In the similarity determination step S34, in a case where the degree of similarity between the endoscope image 38 and the standard image 39 is equal to or greater than the threshold value, a determination result is Yes. In a case where the determination result is Yes, the procedure progresses to the endoscope image saving step S36. In the endoscope image saving step S36, the image transmission unit 58 transmits the image to the image storage unit 48.

On the other hand, in the similarity determination step S34, in a case where the degree of similarity between the endoscope image 38 and the standard image 39 is less than the threshold value, the determination result is No. In a case where the determination result is No, the saving processing unit 53 ends the saving processing step S16.

[Advantageous Effects of Image Processing Device and Method According to First Embodiment]

With the image processing device and method configured as described above, the following advantageous effects can be obtained.

<1>

The endoscope images 38 that are hardly recognized by the scene-of-interest recognition unit 51 are automatically collected. With this, it is possible to improve the performance of the scene-of-interest recognition unit 51 by performing machine learning using the collected endoscope images 38. Furthermore, it is possible to improve the accuracy of recognition of the scene of interest including a lesion or the like from the endoscope image 38.

<2>

The scene-of-interest recognition unit 51 selects the standard image 39 from among the standard image candidates 39a unrecognizable as the scene of interest. With this, the scene-of-interest recognition unit 51 can collect the endoscope images 38, which are hardly recognized by the scene-of-interest recognition unit 51, based on the standard image 39 unrecognizable as the scene of interest.

<3>

Determination is performed whether or not the endoscope image 38 and the standard image 39 are similar using the degree of similarity between the endoscope image 38 and the standard image 39. With this, it is possible to calculate the degree of similarity between the endoscope image 38 and the standard image 39 regardless of a result of recognition of the scene of interest of the endoscope image 38, and to compare both images.

<4>

The degree of similarity with the standard image 39 is calculated based on the feature quantity of the endoscope image 38. With this, it is possible to calculate the degree of similarity with the standard image 39 for a featured part in the endoscope image 38, such as a lesion.

<5>

The degree of similarity with the endoscope image 38 is calculated based on the feature quantity of the standard image 39. With this, it is possible to calculate the degree of similarity with the endoscope image 38 for a featured part in the standard image 39, such as a lesion.

<6>

A lesion is set as a feature of the scene of interest. With this, the endoscope image 38 including a lesion hardly recognized can be automatically collected.

<7>

The standard image 39 is selected from among the endoscope images 38 saved in advance. With this, it is possible to select the standard image 39 unrecognizable as the scene of interest from among the endoscope images 38 acquired in the past.

[Configuration of Image Processing Device According to Second Embodiment]

Next, an image processing device according to a second embodiment will be described. In the following description, differences of the second embodiment from the first embodiment will be primarily described, and description of common points of the first embodiment and the second embodiment will not be repeated.

[Description of Problem]

The endoscope system 9 includes a mode switching function of switching between a video imaging mode in which the video 38a is captured and a static image capturing mode in which the static image 38c is captured. For example, in a case where the static image capturing instruction unit 32 shown in FIG. 1 is operated, the static image 38c according to the operated timing is captured. Imaging of the static image 38c is performed primarily in a case where a scene including a lesion is found, a case where the distal end part 27 of the endoscope 10 reaches a position of interest, a case where a scene including a treatment mark is found, or the like.

A scene of interest in the listed cases or the like can be recognized using a recognizer learned using machine learning. The practitioner operates the endoscope 10 while confirming an image displayed on the display device 13. The endoscope 10 images a body cavity, and the video 38a captured using the endoscope 10 is transmitted to the processor device 12.

However, in a case where a subject is constantly observed using the endoscope system 9, the same scene is imaged for a given period. Then, in a case where a scene of interest is found, a plurality of static images including the scene of interest can be captured for the given period. In other words, in capturing the static image 38c of the scene of interest, a plurality of static images of the same scene can be captured.

Accordingly, in the image processing device and method according to the second embodiment, in capturing the static image 38c including a feature of the scene of interest, it is possible to capture at least one static image 38c including the feature of the scene of interest without capturing a plurality of static images including the same feature as the scene of interest.

[Outline]

The image processing device and method according to the embodiment automatically select, in a case where a recognizer recognizes a scene of interest, a static image including the feature of the scene of interest and automatically save the static image. In saving the static image, a static image dissimilar to the previously saved static image is differentiated and saved. With this, saving of the same image is suppressed, and various static images including the feature of the scene of interest can be saved.

[Hardware Configuration]

The hardware configuration of the image processing device according to the first embodiment shown in FIG. 2 can be applied as the hardware configuration of the image processing device according to the second embodiment. Here, description of the hardware configuration of the image processing device according to the second embodiment will not be repeated.

[Functions of Image Processing Device]

Figure 8:
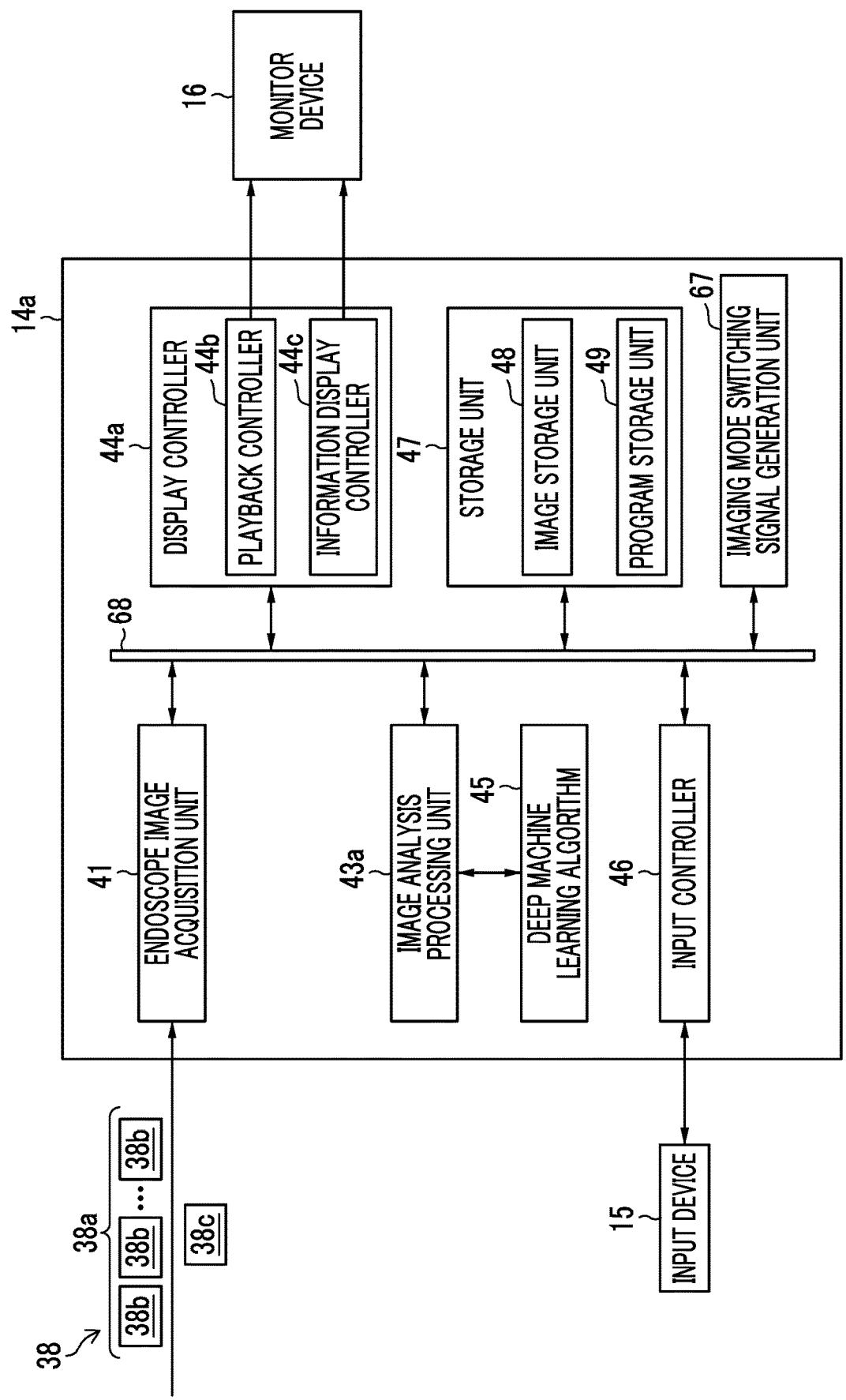
FIG. 8 is a functional block diagram showing functions of an image processing device according to a second embodiment.

FIG. 8 is a functional block diagram showing the functions of the image processing device according to the second embodiment. An image processing device 14a is different from the image processing device 14 shown in FIG. 3 in that the standard image candidate acquisition unit 42 is deleted, and an imaging mode switching signal generation unit 67 is added. Furthermore, the image processing device 14a includes a display controller 44a having the configuration and functions different from the display controller 44 shown in FIG. 3 and an image analysis processing unit 43a having the configuration and functions different from the image analysis processing unit 43 shown in FIG. 3. Each unit will be described below in detail.

<Image Analysis Processing Unit>

Figure 9:
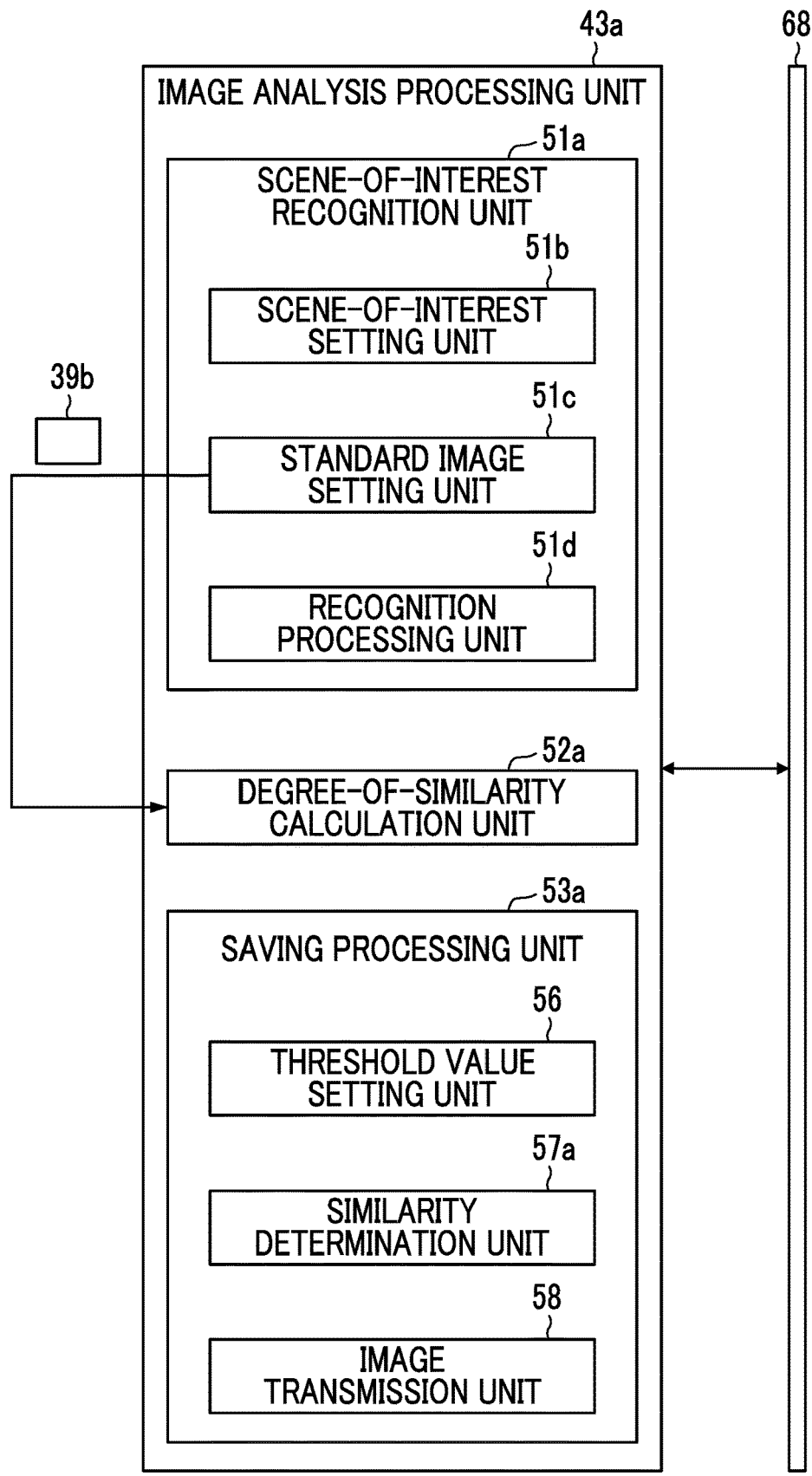
FIG. 9 is a functional block diagram showing functions of an image analysis processing unit shown in FIG. 8.

FIG. 9 is a functional block diagram showing the functions of the image analysis processing unit shown in FIG. 8. The image analysis processing unit 43a shown in FIG. 9 comprises a scene-of-interest recognition unit 51a, a degree-of-similarity calculation unit 52a, and a saving processing unit 53a.

<<Scene-of-Interest Recognition Unit>>

The scene-of-interest recognition unit 51a comprises a scene-of-interest setting unit 51b, a standard image setting unit 51c, and a recognition processing unit 51d.

The scene-of-interest setting unit 51b sets a feature of a scene of interest. Setting of the feature of the scene of interest includes changing of the scene of interest for changing a feature of a previously set scene of interest to a feature of a different scene of interest. The feature of the scene of interest may be automatically set or may be manually set.

The recognition processing unit 51d automatically recognizes the scene of interest from the endoscope image 38. The automatic recognition of the scene of interest is performed by applying a convolutional neural network that performs learning using machine learning. For example, a case where the feature quantity is extracted from the endoscope image 38, and image classification, detection of a part of interest, part classification, and calculation of a degree of similarity are performed based on the extracted feature quantity is considered.

Examples of the feature of the scene of interest include a lesion, a case where the distal end part 27 of the endoscope 10 reaches a position of interest, a treatment mark, and the like. Other examples of the feature of the scene of interest include not only whether or not the entire image is the scene of interest, but also whether or not a lesion reaches a certain stage, whether or not a lesion is detected, whether or not a lesion that reaches a certain stage is detected.

The standard image setting unit 51c sets the standard image 39b that is a static image to be used in determining whether to be similar or dissimilar to the endoscope image 38. The standard image setting unit 51c sets a first static image 38c recognized as the scene of interest as an initial standard image 39b. Hereinafter, the standard image setting unit 51c adds the standard image 39b each time the static image is saved.

<<Degree-of-Similarity Calculation Unit>>

The degree-of-similarity calculation unit 52a calculates the degree of similarity between the static image 38c recognized as the scene of interest and the standard image 39b. The calculation of the degree of similarity is the same as in the first embodiment, and description thereof will not be repeated.

<<Saving Processing Unit>>

The saving processing unit 53a comprises a threshold value setting unit 56, a similarity determination unit 57a, and an image transmission unit 58. The threshold value setting unit 56 sets a threshold value that is used in determining whether or not the static image 38c recognized as the scene of interest and the standard image 39b are similar. The threshold value setting unit 56 is the same as in the first embodiment, and description thereof will not be repeated.

The similarity determination unit 57a classifies the static image 38c recognized as the scene of interest as a target to be saved in a case where the degree of similarity between the static image 38c recognized as the scene of interest and the standard image 39b is equal to or less than the threshold value. The similarity determination unit 57a classifies the static image 38c recognized as the scene of interest as a target to be not saved in a case where the degree of similarity between the static image 38c recognized as the scene of interest and the standard image 39b is greater than the threshold value.

The image transmission unit 58 transmits the endoscope image 38 classified as the target to be saved to the image storage unit 48 shown in FIG. 8. The image transmission unit 58 is the same as in the first embodiment, and description thereof will not be repeated.

<Display Controller>

The display controller 44a shown in FIG. 8 comprises a playback controller 44b and an information display controller 44c. The playback controller 44b and the information display controller 44c will be described below.

<<Playback Controller>>

The playback controller 44b performs display control in displaying the video 38a and the static image 38c on the monitor device 16. The playback controller 44b has the same configuration and functions as the display controller 44 shown in FIG. 3. Here, detailed description of the playback controller 44b will not be repeated.

<<Information Display Controller>>

The information display controller 44c makes the monitor device 16 display notification information. That is, the information display controller 44c generates a signal representing the notification information and transmits the signal representing the notification information to the monitor device 16. The monitor device 16 displays the notification information.

An example of the notification information is static image saving notification information in a case where the static image is saved. Details of static image saving notification will be described below.

<Imaging Mode Switching Signal Generation Unit>

The imaging mode switching signal generation unit 67 generates an imaging mode switching signal in performing switching of an imaging mode of the endoscope 10. The imaging mode switching signal generation unit 67 transmits the imaging mode switching signal to the endoscope system 9. The processor device switches the imaging mode of the endoscope 10 in a case where the imaging mode switching signal is received.

The image processing device 14a according to the embodiment performs imaging of the static image 38c in a case where the scene of interest is recognized from the endoscope image 38 using the scene-of-interest recognition unit 51a. That is, the imaging mode switching signal generation unit 67 generates the imaging mode switching signal in a case where the scene of interest is recognized from the endoscope image 38 and transmits the imaging mode switching signal to the processor device 12.

The static image 38c captured as the scene of interest is transmitted from the processor device 12 to the image processing device 14a. The processor device 12 may comprise a storage device that stores the static image 38c captured as the scene of interest. The imaging mode switching signal generation unit 67 is an example of a component of an imaging mode switching signal transmission unit.

[Procedure of Image Processing Method]

Figure 10:
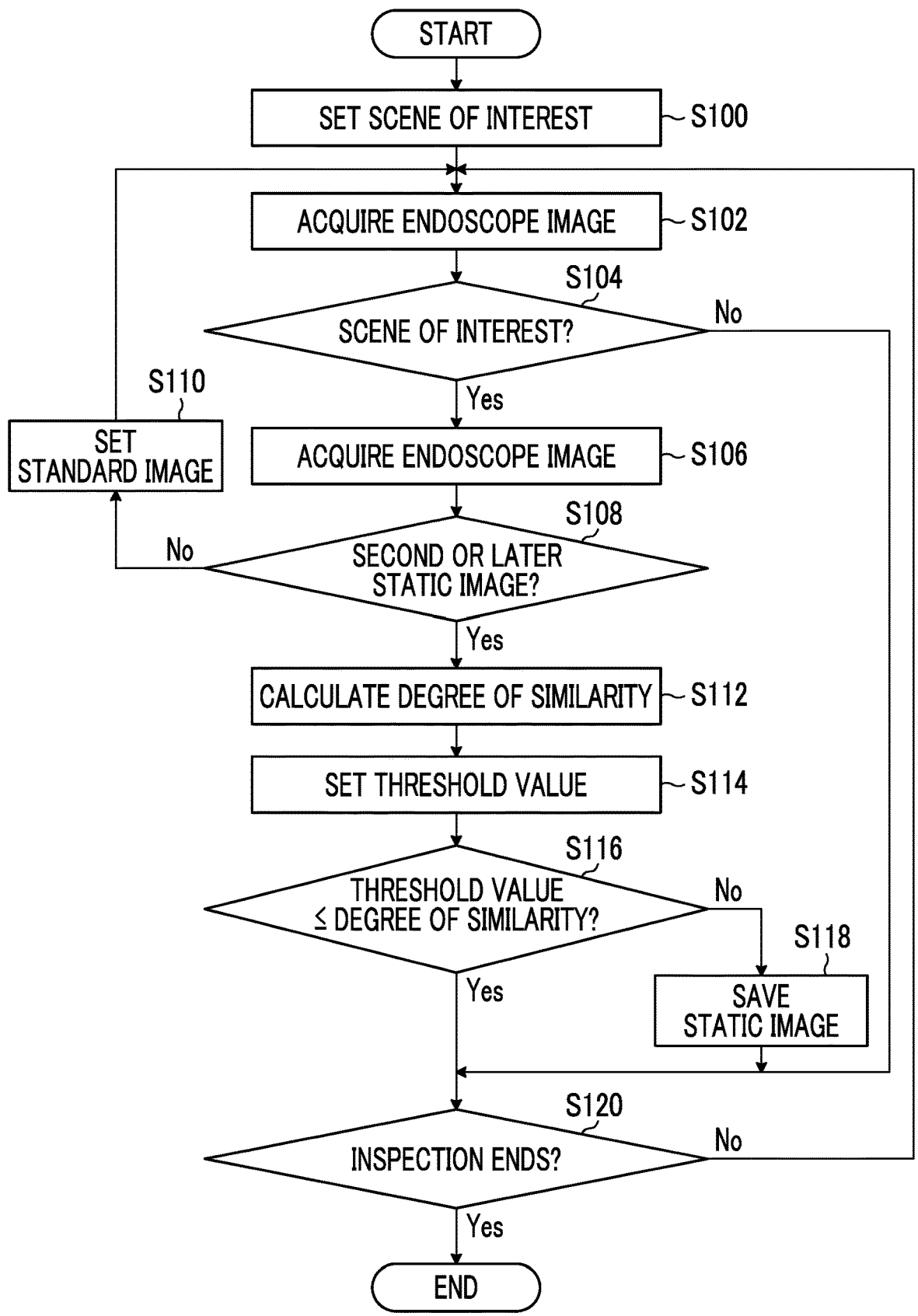
FIG. 10 is a flowchart showing a flow of a procedure of an image processing method according to the second embodiment.

FIG. 10 is a flowchart showing a flow of a procedure of the image processing method according to the second embodiment. A case where the image processing method according to the second embodiment is executed in an endoscopy in which the endoscope 10 connected to the endoscope system 9 is inserted into a body cavity and the endoscope 10 is operated to observe the endoscope image 38 will be described below.

The image processing method is started. First, a scene-of-interest setting step S100 is executed. In the scene-of-interest setting step S100, the scene-of-interest setting unit 51b shown in FIG. 9 sets a feature of a scene of interest. Setting of the feature of the scene of interest stated herein includes changing of the feature of the scene of interest for changing a feature of a previously set scene of interest to a feature of a different scene of interest. The procedure progresses to an endoscope image acquisition step S102 after the scene-of-interest setting step S100.

In the endoscope image acquisition step S102, the scene-of-interest recognition unit 51a acquires the endoscope image 38 acquired using the endoscope 10 through the processor device 12 shown in FIG. 1. That is, in the endoscope image acquisition step S102, the scene-of-interest recognition unit 51a acquires the video 38a as an observation image of the endoscope 10. The endoscope image acquisition step S102 is an example of a medical image acquisition step.

In a scene-of-interest recognition step S104, the scene-of-interest recognition unit 51a determines whether or not the feature of the scene of interest is included for each frame image 38b of the video 38a. The scene-of-interest recognition unit 51a may determine whether or not the feature of the scene of interest is included for the frame image 38b for each prescribed number of frames of the video 38a.

In the scene-of-interest recognition step S104, in a case where an arbitrary frame image 38b does not correspond to the scene of interest, a determination result is No. In a case where the determination result is No, the procedure progresses to an image processing end determination step S120. On the other hand, in the scene-of-interest recognition step S104, in a case where an arbitrary frame image 38b corresponds to the scene of interest, the determination result is Yes. In a case where the determination result is Yes, the procedure progresses to a static image acquisition step S106.

In the static image acquisition step S106, the imaging mode switching signal generation unit 67 shown in FIG. 8 transmits an imaging mode switching signal for switching from the video imaging mode to the static image capturing mode to the endoscope system 9.

The endoscope system 9 that receives the imaging mode switching signal for switching from the video imaging mode to the static image capturing mode performs imaging of the static image 38c. The image analysis processing unit 43a acquires the static image 38c. The procedure progresses to a number-of-captured images determination step S108 after the static image acquisition step S106.

In the number-of-captured images determination step S108, the standard image setting unit 51c determines whether the captured static image 38c is a first image or a second image or later. In a case where the captured static image 38c is the first image, a determination result is No. In a case where the determination result is No, the procedure progresses to a standard image setting step S110. In the standard image setting step S110, the standard image setting unit 51c sets the captured static image 38c as the standard image 39b. The image transmission unit 58 transmits the static image 38c set as the standard image 39b to the image storage unit 48. The procedure progresses to the endoscope image acquisition step S102 after the standard image setting step S110.

On the other hand, in a case where the captured static image 38*c* is the second image or later, the determination result is Yes. In a case where the determination result is Yes, the procedure progresses to a degree-of-similarity calculation step S112. In a case where the determination result of the number-of-captured images determination step S108 is Yes, the procedure may progress to the degree-of-similarity calculation step S112 after a standard image addition step of adding the second static image 38*c* or later to the standard image 39*b*.

In the degree-of-similarity calculation step S112, the degree-of-similarity calculation unit 52*a* calculates the degree of similarity between the captured static image 38*c* and the standard image 39*b*. The degree-of-similarity calculation step S112 is a step of executing the same processing as in the degree-of-similarity calculation step S14 shown in FIG. 5. Here, description of the degree-of-similarity calculation step S112 will not be repeated. The procedure progresses to a threshold value setting step S114 after the degree-of-similarity calculation step S112.

In the threshold value setting step S114, the threshold value setting unit 56 sets a threshold value that is used in determining whether the captured static image 38*c* and the standard image 39*b* are similar or dissimilar. The threshold value setting step S114 is the same step as the threshold value setting step S30 shown in FIG. 7. Here, description of the threshold value setting step S114 will not be repeated. The procedure progresses to a similarity determination step S116 after the threshold value setting step S114.

In the similarity determination step S116, the similarity determination unit 57*a* determines whether or not the degree of similarity calculated in the degree-of-similarity calculation step S112 is greater than the threshold value. In a case where the degree of similarity is equal to or less than the threshold value, a determination result is No. In a case where the determination result is No, the procedure progresses to a static image saving step S118. That is, in a case where the captured static image 38*c* and the standard image 39*b* are dissimilar, the captured static image 38*c* is saved.

In the static image saving step S118, the image transmission unit 58 transmits the static image 38*c* to be a target to be saved to the image storage unit 48. Furthermore, in the static image saving step S118, the standard image setting unit 51*c* adds the static image 38*c* to be a target to be saved as the standard image 39*b*.

The procedure progresses to the image processing end determination step S120 after the static image saving step S118. The threshold value setting step S114, the similarity determination step S116, and the static image saving step S118 are the components of the saving processing step.

In the image processing end determination step S120, the image analysis processing unit 43*a* determines whether or not the endoscopy ends. In a case where the endoscopy ends, a determination result is No. In a case where the determination result is No, the procedure progresses to the endoscope image acquisition step S102. Hereinafter, the steps of the endoscope image acquisition step S102 to the image processing end determination step S120 are repeatedly executed until the determination result of the image processing end determination step S120 is Yes.

On the other hand, in a case where the endoscopy ends, the determination result is Yes. In a case where the determination result is Yes, the image processing method ends.

[Example of Saving of Standard Image]

In saving the standard image 39*b*, the feature quantity may be extracted from the standard image 39*b*, and the feature quantity may be saved. Both of the standard image 39*b* and the feature quantity of the standard image 39*b* may be saved. This is useful in a case where the feature quantities of the static image 38*c* and the standard image 39*b* are used in calculating the degree of similarity between the static image 38*c* and the standard image 39*b*.

[Example of Static Image to be Target to be Saved]

First Example

Figure 11:
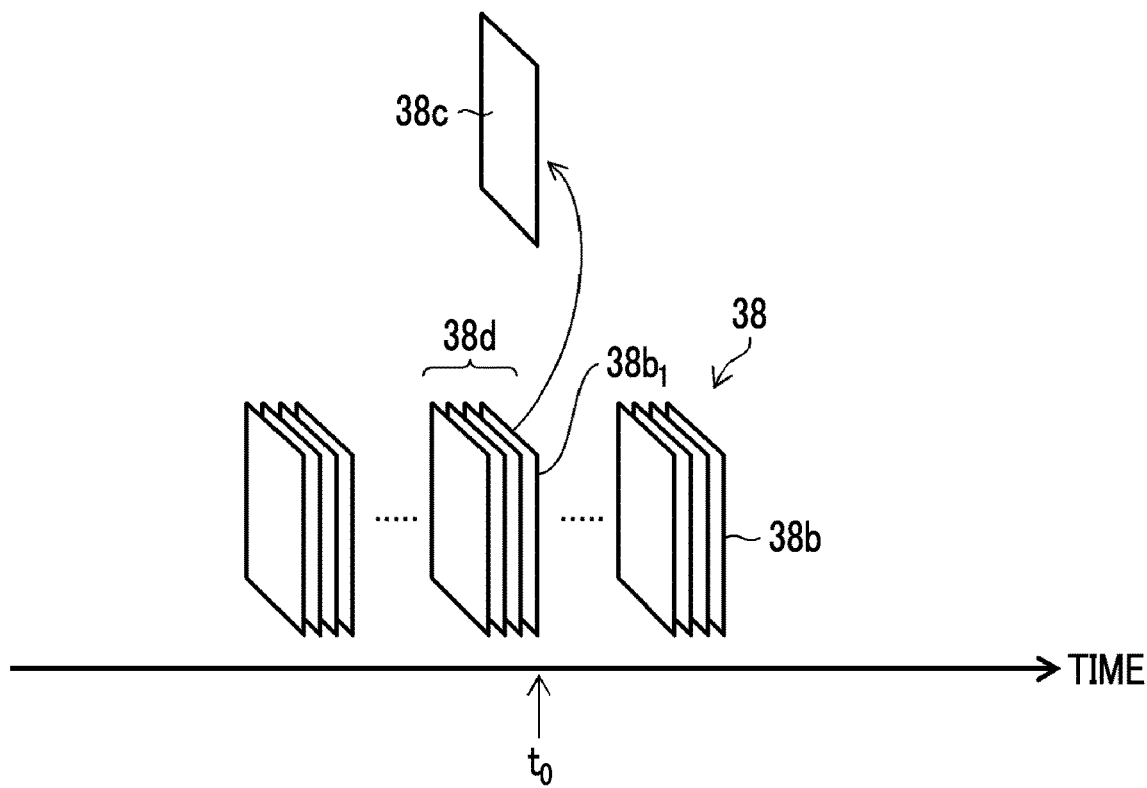
FIG. 11 is a schematic view showing an example of a static image to be saved.

FIG. 11 is a schematic view showing an example of a static image to be a target to be saved. In the example shown in FIG. 11, a frame image 38*b*$_1$ at a timing to when the scene of interest is recognized becomes the static image 38*c* to be a target to be saved. The frame image 38*b*$_1$ at the timing to when the scene of interest is recognized is an example of a medical image recognized as a scene of interest.

In acquiring the frame image 38*b*$_1$, a plurality of frame images 38*d* following the frame image 38*b*$_1$ may be acquired. In other words, in a case where the scene of interest is recognized from the endoscope image 38, a plurality of frame images 38*d* for a given period from the timing to when the scene of interest is recognized may be acquired, and one representative frame image 38*b* may be selected from among a plurality of frame images 38*d*.

Second Example

Figure 12:
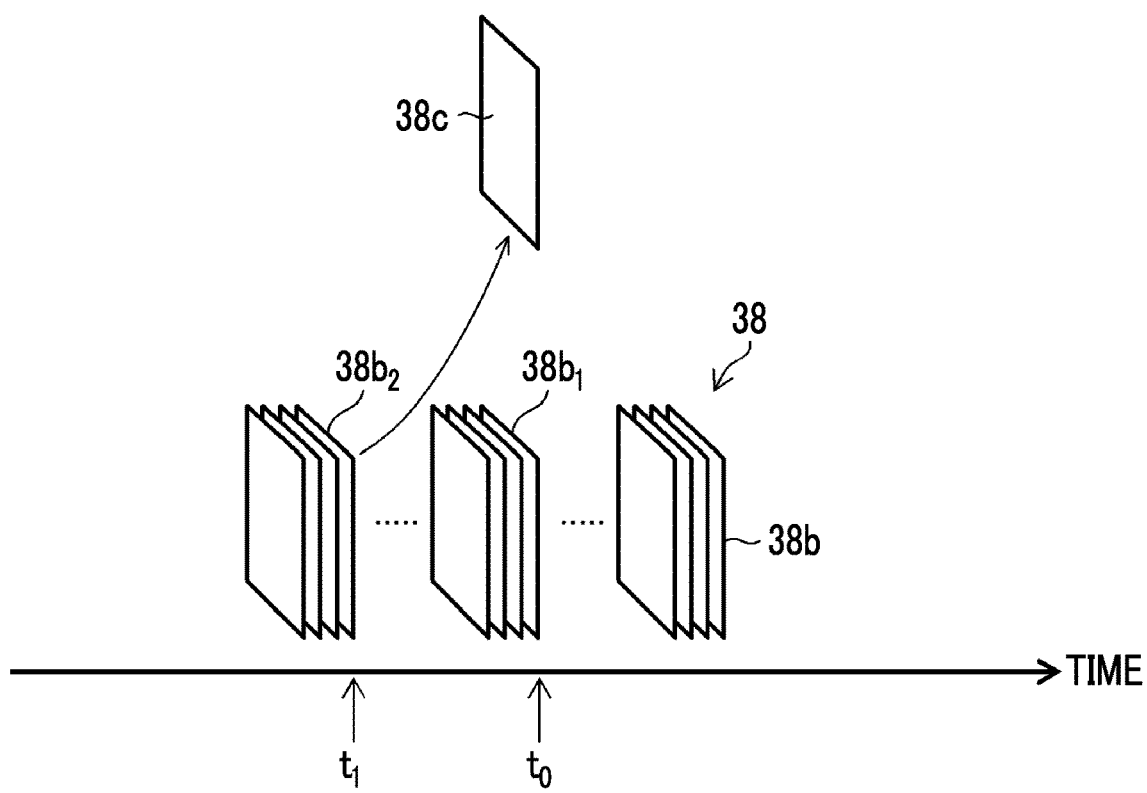
FIG. 12 is a schematic view showing another example of a static image to be saved.

FIG. 12 is a schematic view showing another example of a static image to be a target to be saved. In the example shown in FIG. 12, an example where a frame image 38*b*$_2$ at a timing $t_1$ after a given period from the timing to when the scene of interest is recognized is saved as the static image 38*c* is shown. The period from the timing $t_0$ to the timing $t_1$ is determined according to a speed of the endoscope 10 and a frame rate in capturing the video 38*a*.

It is considered that the same scene is imaged for the given period from the timing to when the scene of interest is recognized. Then, in a case of performing manual static image capturing, a delay period until the practitioner performs an imaging operation after recognizing the feature of the scene of interest and a delay period from the imaging operation to actual acquisition of the static image 38*c* occur.

Then, in a case where the frame image 38*b*$_2$ after the given period corresponding to the above-described delay period from the timing to when the scene of interest is recognized is saved as the static image 38*c*, the same static image 38*c* as in manual static image capturing can be acquired. The frame image 38*b*2 at the timing $t_1$ after the given period from the timing to when the scene of interest is recognized is an example of a medical image acquired after the medical image recognized as the scene of interest.

Next, static image saving notification in a case where the static image is saved will be described. The image processing device and method according to the second embodiment perform notification using the monitor device 16 in a case where the static image 38*c* is saved.

First Example

Figure 13:
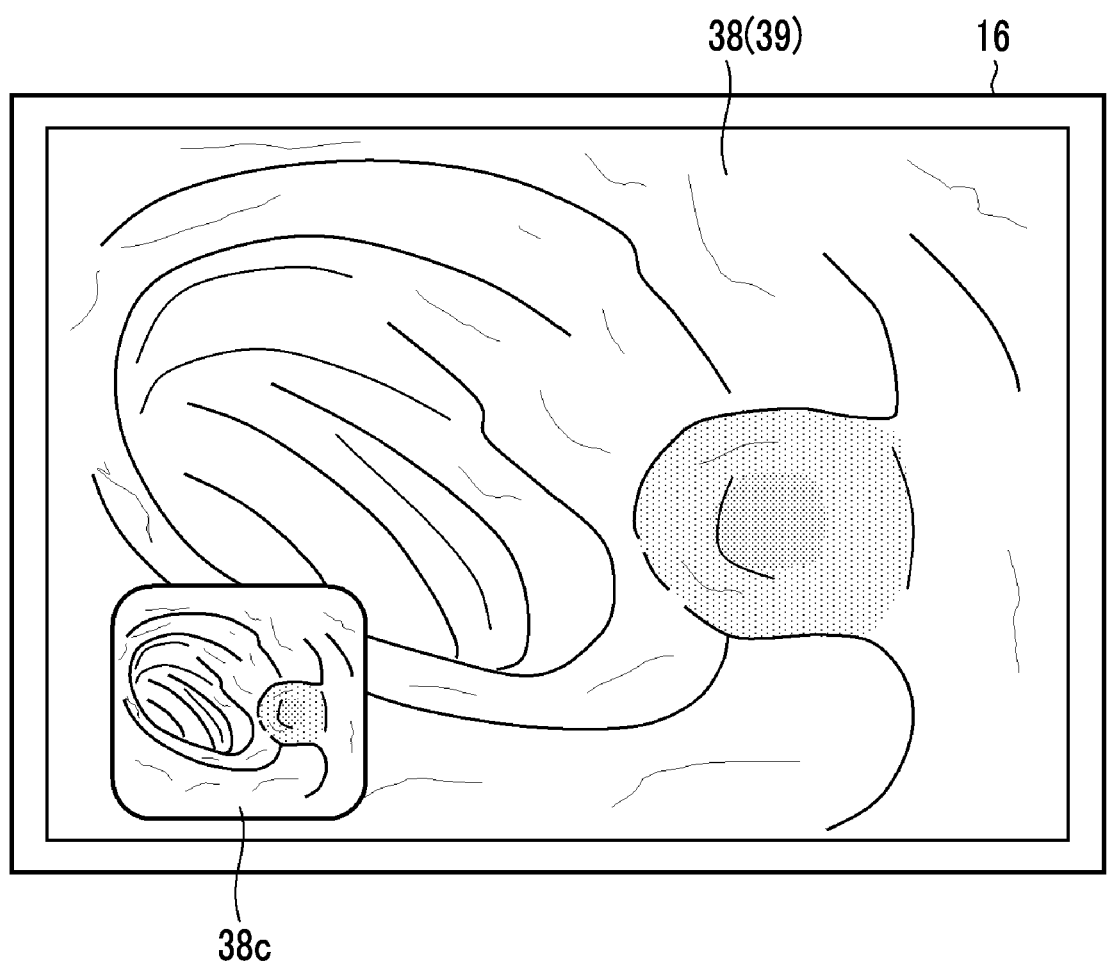
FIG. 13 is a configuration diagram of a display screen showing a first example of static image saving notification.

FIG. 13 is a configuration diagram of a display screen showing a first example of static image saving notification. FIG. 13 shows an example where the static image 38*c* saved using the image storage unit 48 is displayed on a display screen of the endoscope image 38 in a superimposed manner.

That is, in a case where the static image 38c that is recognized as the scene of interest and is dissimilar to the previously saved static image 38c is saved, the information display controller 44c shown in FIG. 8 transmits a display signal representing the saved static image 38c to the monitor device 16.

It is preferable that the static image 38c that is displayed on the display screen of the endoscope image 38 in a superimposed manner is displayed at a position not to be an obstacle to observation of the endoscope image 38 on a reduced scale. The information display controller 44c is an example of a component of a notification unit.

Second Example

Figure 14:
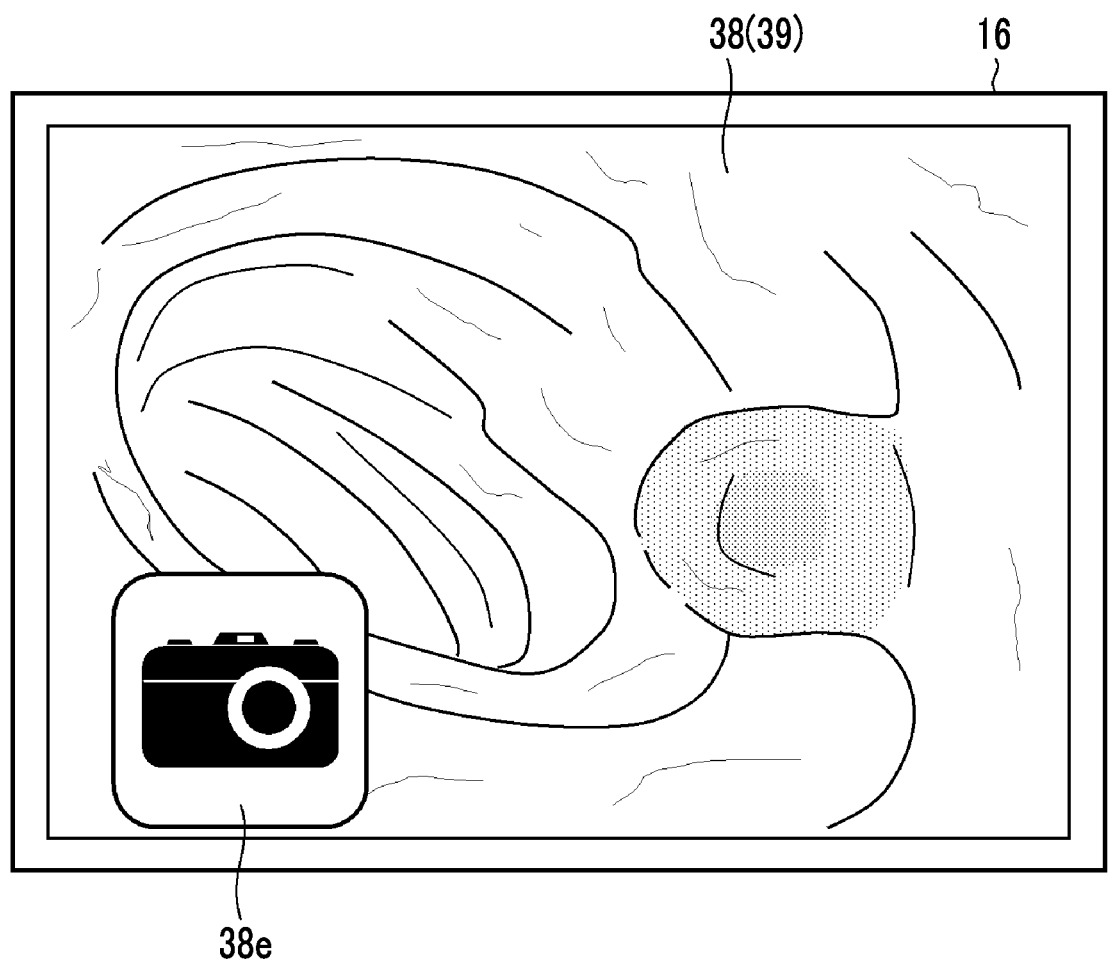
FIG. 14 is a configuration diagram of a display screen showing a second example of static image saving notification.

FIG. 14 is a configuration diagram of a display screen showing a second example of static image saving notification. FIG. 14 shows an example where an icon 38e representing the static image is saved is displayed on the display screen of the endoscope image 38 in a superimposed manner for a given period.

<Example of Other Static Image Saving Notification>

Examples of other static image saving notification include an example where the endoscope image 38 is frozen for a given period. Static image saving notification using sound, such as notification sound or voice, can also be performed.

[Advantageous Effects of Image Processing Device and Method According to Second Embodiment]

With the image processing device and method configured as described above, the following advantageous effects can be obtained.

<1>

The static image 38c that is dissimilar to the previously saved static image 38c is saved. With this, saving of a similar static image 38c of the same scene is avoided.

<2>

In a case where the scene of interest is recognized, the imaging mode switching signal for switching the imaging mode of the endoscope 10 from the video imaging mode to the static image capturing mode is generated, and the imaging mode switching signal is transmitted to the endoscope system 9. With this, in a case where the scene of interest is recognized, static image capturing is automatically performed.

<3>

The frame image 38b at the timing $t_1$ after the given period from the timing to when the scene of interest is recognized is saved as the static image 38c. With this, it is possible to save the frame image 38b at the same timing as manual imaging as the static image 38c.

<4>

Notification is performed in a case where the static image 38c is saved. With this, the practitioner can recognize that the static image 38c is saved.

[Application Example of Image Processing Device]

As an application example of the image processing device, the image analysis processing unit 43 shown in FIG. 3 or the image analysis processing unit 43a shown in FIG. 8 are integrated into the processor device 12 shown in FIG. 1. That is, a function of performing processing for automatically capturing the static image 38c in a case where the scene of interest is recognized and automatically differentiating the captured static image 38c can be added to the processor device 12 that performs imaging control of the endoscope 10 and performs processing of an image signal acquired from the endoscope 10.

[Modification Example of Endoscope System]

[Modification Example of Illumination Light]

An example of a medical image that can be acquired using the endoscope system 9 shown in the embodiment is a normal light image that is obtained through irradiation of light in a white range or light in a plurality of wavelength ranges as light in the white range.

Another example of a medical image that can be acquired using the endoscope system 9 shown in the embodiment is an image obtained through irradiation of light in a specific wavelength range. The specific wavelength range can be a range narrower than the white range. The following modification examples can be applied.

First Example

A first example of the specific wavelength range is a blue range or a green range of a visible range. In the wavelength range of the first example includes a wavelength range of 390 nanometers to 450 nanometers or a wavelength range of 530 nanometers to 550 nanometers, and light of the first example has a peak wavelength in the wavelength range of 390 nanometers to 450 nanometers or the wavelength range of 530 nanometers to 550 nanometers.

Second Example

A second example of the specific wavelength range is a red range of a visible range. The wavelength range of the second example includes a wavelength range of 585 nanometers to 615 nanometers or a wavelength range of 610 nanometers to 730 nanometers, and light of the second example has a peak wavelength in the wavelength range of 585 nanometers to 615 nanometers or the wavelength range of 610 nanometers to 730 nanometers.

Third Example

A third example of the specific wavelength range includes a wavelength range in which light absorption coefficients of oxygenated hemoglobin and reduced hemoglobin are different, and light of the third example has a peak wavelength in the wavelength range in which the light absorption coefficients of oxygenated hemoglobin and reduced hemoglobin are different. The wavelength range of the third example includes a wavelength range of 400±10 nanometers, a wavelength range of 440±10 nanometers, a wavelength range 470±10 nanometers, or a wavelength range of 600 nanometers to 750 nanometers, and light of the third example has a peak wavelength in the wavelength range of 400±10 nanometers, the wavelength range of 440±10 nanometers, the wavelength range of 470±10 nanometers, or the wavelength range of 600 nanometers to 750 nanometers.

Fourth Example

A fourth example of the specific wavelength range is a wavelength range of excitation light that is used to observe fluorescence emitted from a fluorescent material in a living body and excites the fluorescent material. For example, the specific wavelength range is a wavelength range of 390 nanometers to 470 nanometers. Observation of fluorescence may be referred to as fluorescence observation.

Fifth Example

A fifth example of the specific wavelength range is a wavelength range of infrared light. The wavelength range of the fifth example includes a wavelength range of 790 nanometers to 820 nanometers or a wavelength range of 905 nanometers to 970 nanometers, and light of the fifth example has a peak wavelength in the wavelength range of 790 nanometers to 820 nanometers or the wavelength range of 905 nanometers to 970 nanometers.

[Generation Example of Special Light Image]

The processor device 12 may generate a special light image having information of a specific wavelength range based on a normal light image obtained through imaging using white light. The term "generation" stated herein includes acquisition. In this case, the processor device 12 functions as a special light image acquisition unit. Then, the processor device 12 obtains a signal of the specific wavelength range by performing an arithmetic operation based on color information of red, green, and blue or cyan, magenta, and yellow included in the normal light image.

Red, green, and blue may be represented by RGB (Red, Green, Blue). Furthermore, cyan, magenta, and yellow may be represented by CMY (Cyan, Magenta, Yellow).

[Generation Example of Feature Quantity Image]

As a medical image, a feature quantity image can be generated using an arithmetic operation based on at least one of a normal image obtained through irradiation of light in a white range or light in a plurality of wavelength ranges as light in the white range or a special light image obtained through irradiation of light in a specific wavelength range.

[Application Example to Program Causing Computer to Function as Image Processing Device]

The above-described image processing method can be configured as a program that implements the functions corresponding to the respective steps in the image processing method using a computer. For example, a program that causes the computer to implement an endoscope image acquisition function, an image analysis processing function, an input control function, a display control function, and a storage function can be configured.

The endoscope image acquisition function is an example of a medical image acquisition function. The image analysis processing function includes, as components, a scene-of-interest recognition function, a degree-of-similarity calculation function, and a saving processing function.

A program that causes a computer to implement the above-described image processing function can be recorded on a computer readable medium, such as an optical disk, a magnetic disk, a semiconductor memory, or other tangible and non-transitory information storage mediums, and the program can be provided through the information storage medium. Instead of the aspect in which the program is provided while being stored in the tangible and non-transitory information storage medium, program signals may be provided as a download service through a telecommunication line, such as the Internet.

Furthermore, instead of the aspect in which the program is provided while being stored in the non-transitory information storage medium, an aspect in which program signals are provided through a network may be made.

[For Combinations of Embodiments and Modification Examples]

The components described in the above-described embodiments and the components described in the above-described modification examples may be appropriately combined with each other, and some of components may be substituted.

In the above-described embodiments of the invention, the components may be appropriately changed, added, or deleted without departing from the scope of the invention. The invention is not limited to the above-described embodiments and may be modified in various ways by those skilled in the art within the technical scope and spirit of the invention.

EXPLANATION OF REFERENCES

1: controller
2: memory
3: hard disk device
4: communication interface
5: input controller
6: display controller
9: endoscope system
10: endoscope
11: light source device
12: processor device
13: display device
14, 14a: image processing device
15: input device
16: monitor device
17: network
18: storage device
19: standard image candidate saving unit
20: insertion part
21: operating part
22: universal cord
25: flexible part
26: bending part
27: distal end part
27a: distal end surface
28: imaging element
29: bending operation knob
30: air supply and water supply button
31: suction button
32: static image capturing instruction unit
33: treatment tool inlet
35: light guide
36: signal cable
37a, 37b: connector
38: endoscope image
38a: video
38b: frame image
38c: static image
38d: a plurality of frame images
38e: icon
39, 39b: standard image
39a: standard image candidate
40: overall controller
41: endoscope image acquisition unit
42: standard image candidate acquisition unit
43, 43a: image analysis processing unit
44, 44a: display controller
44b: playback controller
44c: information display controller
45: deep machine learning algorithm
46: input controller
47: storage unit
48: image storage unit
49: program storage unit
51, 51a: scene-of-interest recognition unit 51b: scene-of-interest setting unit
51c: standard image setting unit
51d: recognition processing unit
52, 52a: degree-of-similarity calculation unit
53, 53a: saving processing unit
54: standard image selection unit
55: standard image saving processing unit
56: threshold value setting unit
57, 57a: similarity determination unit
58: image transmission unit
67: imaging mode switching signal generation unit
68: communication signal line
c: constant
D: degree of similarity
$t_0$, $t_1$: timing
S10 to S120: steps of image processing method

What is claimed is:

1. An image processing device comprising a processor configured to:
    acquire a standard image saved in advance in a memory, and the standard image being selected from a plurality of medical images in which scenes of interests are unrecognized by a recognizer;
    acquire a medical image captured by an endoscope;
    calculate a degree of similarity between the medical image captured by the endoscope and the standard image saved in advance in the memory;
    execute processing for saving the medical image in the memory based on the degree of similarity; and
    save the medical image captured by the endoscope in the memory in a case where the degree of similarity between the standard image saved in advance in the memory and the medical image captured by the endoscope is equal to or greater than a prescribed threshold value.

2. The image processing device according to claim 1, wherein the processor is further configured to:
    extract a feature quantity from the medical image,
    wherein the calculate the degree of similarity between the medical image and the standard image based on the feature quantity of the medical image.

3. The image processing device according to claim 1, wherein the processor is further configured to:
    extract a feature quantity from the standard image.

4. The image processing device according to claim 1,
    wherein the processor is further configured to acquire a feature quantity of the standard image,
    wherein the processor calculates the degree of similarity between the medical image and the standard image based on a feature quantity of the medical image and the feature quantity of the standard image.

5. The image processing device according to claim 1, wherein the processor recognizes a scene including a lesion as the scenes of interests.

6. The image processing device according to claim 1,
    wherein the processor selects the standard image from among the plurality of medical images unrecognized as the scenes of interests using a comparison result of the plurality of medical images unrecognized as the scenes of interests and a correct answer image of a medical image hardly recognized, and
    the processor saves the plurality of medical images in the memory in a case where the degree of similarity is equal to or greater than the prescribed threshold value.

7. The image processing device according to claim 1, wherein the processor gives notification of saving of the medical image in the saving device memory.

8. An image processing device comprising a processor configured to:
    acquire a plurality of medical images saved in advance in a memory;
    acquire a medical image captured by an endoscope;
    calculate a degree of similarity between the medical image captured by the endoscope and the plurality of medical images saved in advance in the memory; and
    save the medical image captured by the endoscope in the memory in a case where the degree of similarity between the medical image captured by the endoscope and the plurality of medical images saved in advance in the memory is equal to or less than a prescribed threshold value.

9. The image processing device according to claim 8,
    wherein the processor transmits a switching signal for switching an imaging mode of an endoscope from a video imaging mode to a static image capturing mode to an endoscope device comprising the endoscope in a case where a scene of interest from the medical image is recognized.

10. The image processing device according to claim 8,
    wherein the processor saves the medical image recognized as a scene of interest in the memory.

11. The image processing device according to claim 8,
    wherein the processor saves the medical image acquired after the medical image recognized as a scene of interest in the memory.

12. The image processing device according to claim 8,
    wherein the processor sets a first medical image recognized as a scene of interest as the standard image.

13. An endoscope system comprising:
    an endoscope device that comprises an endoscope; and
    an image processing device,
    wherein the image processing device comprises a processor configured to:
        acquire a standard image saved in advance in a memory, and the standard image being selected from a plurality of medical images in which scenes of interests are unrecognized by a recognizer;
        acquire a medical image captured by an endoscope;
        calculate a degree of similarity between the medical image captured by the endoscope and the standard image saved in advance in the memory;
        save the medical image captured by the endoscope in the memory in a case where the degree of similarity between the standard image saved in advance in the memory and the medical image captured by the endoscope is equal to or greater than a prescribed threshold value.

14. An image processing method comprising:
    acquiring a standard image saved in advance in a memory, and the standard image being selected from a plurality of medical images in which scenes of interests are unrecognized by a recognizer;
    acquiring a medical image captured by an endoscope;
    calculating a degree of similarity between the medical image captured by the endoscope and standard image saved in advance in the memory;
    saving the medical image captured by the endoscope in the memory in a case where the degree of similarity between the standard image saved in advance in the memory and the medical image captured by the endoscope is equal to or greater than a prescribed threshold value.

15. A non-transitory, tangible computer readable recording medium that, in a case where a command stored in the recording medium is read by a computer, causes the computer to implement:
    acquiring a standard image saved in advance in a memory, and the standard image being selected from a plurality of medical images in which scenes of interests are unrecognized by a recognizer;
    acquiring a medical image captured by an endoscope;
    calculating a degree of similarity between the medical image captured by the endoscope and the standard image saved in advance in the memory; and
    saving the medical image captured by the endoscope in the memory in a case where the degree of similarity between the standard image saved in advance in the memory and the medical image captured by the endoscope is equal to or greater than a prescribed threshold value.

* * * * *